(12) United States Patent
Heiliger et al.

(10) Patent No.: US 12,030,195 B2
(45) Date of Patent: Jul. 9, 2024

(54) TENSIONING MECHANISMS AND METHODS FOR ARTICULATING SURGICAL INSTRUMENTS SUCH AS FOR USE IN ROBOTIC SURGICAL SYSTEMS

(71) Applicant: Covidien LP, Mansfield, MA (US)

(72) Inventors: Zachary S. Heiliger, Nederland, CO (US); Kurt J. Anglese, Lafayette, CO (US); Ian M. Anderson, Louisville, CO (US); Crystal A. Adams, Westminster, CO (US); Jeremy P. Green, Westminster, CO (US); Russell W. Holbrook, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1000 days.

(21) Appl. No.: 16/884,653

(22) Filed: May 27, 2020

(65) Prior Publication Data

US 2021/0369368 A1   Dec. 2, 2021

(51) Int. Cl.
*A61B 17/00* (2006.01)
*B25J 9/16* (2006.01)

(52) U.S. Cl.
CPC ... *B25J 9/1689* (2013.01); *A61B 2017/00323* (2013.01)

(58) Field of Classification Search
CPC .......... B25J 9/1689; A61B 2017/00323; A61B 18/1442; A61B 2017/00477;
(Continued)

(56) References Cited

U.S. PATENT DOCUMENTS

| 4,688,555 A | 8/1987 | Wardle |
| 5,752,973 A | 5/1998 | Kieturakis |

(Continued)

FOREIGN PATENT DOCUMENTS

| EP | 2415418 A1 | 2/2012 |
| WO | 2017136710 A2 | 8/2017 |
| WO | 2017205311 A1 | 11/2017 |

OTHER PUBLICATIONS

Partial European Search Report issued in corresponding European Application No. 21176129.1 dated Oct. 22, 2021, 15 pages.
(Continued)

*Primary Examiner* — Yingchuan Zhang
*Assistant Examiner* — Sebastian X Lukjan
(74) *Attorney, Agent, or Firm* — Carter, DeLuca & Farrell LLP

(57) ABSTRACT

An articulation assembly for a robotic surgical instrument includes a plurality of rotatable but longitudinally fixed lead screws extending between first and second base plates, a collar threaded about each lead screws and configured to translate therealong in response to rotation of the corresponding lead screw, an articulation cable coupled to each collar and defining or having a threaded shaft, and a threaded nipple threaded about each of the threaded shafts. Each threaded nipple is engaged with one of the collars to thereby engage each of the articulation cables with a corresponding one of the collars such that longitudinal translation of the corresponding collar pushes or pulls the corresponding articulation cable. Each threaded nipple is configured for further threading or unthreading about the corresponding threaded shaft to vary a pre-tension on the corresponding articulation cable.

19 Claims, 14 Drawing Sheets

(58) Field of Classification Search
CPC ............ A61B 2018/1452; A61B 34/37; A61B 2034/715; A61B 34/71; A61B 2034/302; A61B 34/30; A61N 7/00
See application file for complete search history.

(56) References Cited

U.S. PATENT DOCUMENTS

| | | | |
|---|---|---|---|
| 5,784,542 | A | 7/1998 | Ohm et al. |
| 5,792,135 | A | 8/1998 | Madhani et al. |
| 5,848,986 | A | 12/1998 | Lundquist et al. |
| 6,132,368 | A | 10/2000 | Cooper |
| 6,206,903 | B1 | 3/2001 | Ramans |
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll et al. |
| 6,671,581 | B2 | 12/2003 | Niemeyer et al. |
| 6,676,684 | B1 | 1/2004 | Morley et al. |
| 6,685,698 | B2 | 2/2004 | Morley et al. |
| 6,699,235 | B2 | 3/2004 | Wallace et al. |
| 6,714,839 | B2 | 3/2004 | Salisbury, Jr. et al. |
| 6,716,233 | B1 | 4/2004 | Whitman |
| 6,728,599 | B2 | 4/2004 | Wang et al. |
| 6,746,443 | B1 | 6/2004 | Morley et al. |
| 6,766,204 | B2 | 7/2004 | Niemeyer et al. |
| 6,770,081 | B1 | 8/2004 | Cooper et al. |
| 6,772,053 | B2 | 8/2004 | Niemeyer |
| 6,783,524 | B2 | 8/2004 | Anderson et al. |
| 6,793,652 | B1 | 9/2004 | Whitman et al. |
| 6,793,653 | B2 | 9/2004 | Sanchez et al. |
| 6,799,065 | B1 | 9/2004 | Niemeyer |
| 6,817,974 | B2 | 11/2004 | Cooper et al. |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,843,403 | B2 | 1/2005 | Whitman |
| 6,846,309 | B2 | 1/2005 | Whitman et al. |
| 6,866,671 | B2 | 3/2005 | Tierney et al. |
| 6,871,117 | B2 | 3/2005 | Wang et al. |
| 6,879,880 | B2 | 4/2005 | Nowlin et al. |
| 6,899,705 | B2 | 5/2005 | Niemeyer |
| 6,902,560 | B1 | 6/2005 | Morley et al. |
| 6,936,042 | B2 | 8/2005 | Wallace et al. |
| 6,951,535 | B2 | 10/2005 | Ghodoussi et al. |
| 6,974,449 | B2 | 12/2005 | Niemeyer |
| 6,991,627 | B2 | 1/2006 | Madhani et al. |
| 6,994,708 | B2 | 2/2006 | Manzo |
| 7,048,745 | B2 | 5/2006 | Tierney et al. |
| 7,066,926 | B2 | 6/2006 | Wallace et al. |
| 7,118,582 | B1 | 10/2006 | Wang et al. |
| 7,125,403 | B2 | 10/2006 | Julian et al. |
| 7,155,315 | B2 | 12/2006 | Niemeyer et al. |
| 7,239,940 | B2 | 7/2007 | Wang et al. |
| 7,306,597 | B2 | 12/2007 | Manzo |
| 7,357,774 | B2 | 4/2008 | Cooper |
| 7,373,219 | B2 | 5/2008 | Nowlin et al. |
| 7,379,790 | B2 | 5/2008 | Toth et al. |
| 7,386,365 | B2 | 6/2008 | Nixon |
| 7,391,173 | B2 | 6/2008 | Schena |
| 7,398,707 | B2 | 7/2008 | Morley et al. |
| 7,413,565 | B2 | 8/2008 | Wang et al. |
| 7,453,227 | B2 | 11/2008 | Prisco et al. |
| 7,524,320 | B2 | 4/2009 | Tierney et al. |
| 7,574,250 | B2 | 8/2009 | Niemeyer |
| 7,594,912 | B2 | 9/2009 | Cooper et al. |
| 7,607,440 | B2 | 10/2009 | Coste-Maniere et al. |
| 7,666,191 | B2 | 2/2010 | Orban, III et al. |
| 7,682,357 | B2 | 3/2010 | Ghodoussi et al. |
| 7,689,320 | B2 | 3/2010 | Prisco et al. |
| 7,695,481 | B2 | 4/2010 | Wang et al. |
| 7,695,485 | B2 | 4/2010 | Whitman et al. |
| 7,699,855 | B2 | 4/2010 | Anderson et al. |
| 7,713,263 | B2 | 5/2010 | Niemeyer |
| 7,725,214 | B2 | 5/2010 | Diolaiti |
| 7,727,244 | B2 | 6/2010 | Orban, III et al. |
| 7,741,802 | B2 | 6/2010 | Prisco et al. |
| 7,756,036 | B2 | 7/2010 | Druke et al. |
| 7,757,028 | B2 | 7/2010 | Druke et al. |
| 7,762,825 | B2 | 7/2010 | Burbank et al. |
| 7,778,733 | B2 | 8/2010 | Nowlin et al. |
| 7,799,028 | B2 | 9/2010 | Schechter et al. |
| 7,803,151 | B2 | 9/2010 | Whitman |
| 7,806,891 | B2 | 10/2010 | Nowlin et al. |
| 7,819,859 | B2 | 10/2010 | Prisco et al. |
| 7,819,885 | B2 | 10/2010 | Cooper |
| 7,824,401 | B2 | 11/2010 | Manzo et al. |
| 7,835,823 | B2 | 11/2010 | Sillman et al. |
| 7,843,158 | B2 | 11/2010 | Prisco |
| 7,861,906 | B2 | 1/2011 | Doll et al. |
| 7,865,266 | B2 | 1/2011 | Moll et al. |
| 7,865,269 | B2 | 1/2011 | Prisco et al. |
| 7,886,743 | B2 | 2/2011 | Cooper et al. |
| 7,899,578 | B2 | 3/2011 | Prisco et al. |
| 7,907,166 | B2 | 3/2011 | Lamprecht et al. |
| 7,918,230 | B2 | 4/2011 | Whitman et al. |
| 7,935,130 | B2 | 5/2011 | Williams |
| 7,963,913 | B2 | 6/2011 | Devengenzo et al. |
| 7,983,793 | B2 | 7/2011 | Toth et al. |
| 8,002,767 | B2 | 8/2011 | Sanchez et al. |
| 8,004,229 | B2 | 8/2011 | Nowlin et al. |
| 8,012,170 | B2 | 9/2011 | Whitman et al. |
| 8,054,752 | B2 | 11/2011 | Druke et al. |
| 8,062,288 | B2 | 11/2011 | Cooper et al. |
| 8,079,950 | B2 | 12/2011 | Stern et al. |
| 8,100,133 | B2 | 1/2012 | Mintz et al. |
| 8,108,072 | B2 | 1/2012 | Zhao et al. |
| 8,120,301 | B2 | 2/2012 | Goldberg et al. |
| 8,142,447 | B2 | 3/2012 | Cooper et al. |
| 8,147,503 | B2 | 4/2012 | Zhao et al. |
| 8,151,661 | B2 | 4/2012 | Schena et al. |
| 8,155,479 | B2 | 4/2012 | Hoffman et al. |
| 8,182,469 | B2 | 5/2012 | Anderson et al. |
| 8,202,278 | B2 | 6/2012 | Orban, III et al. |
| 8,206,406 | B2 | 6/2012 | Orban, III |
| 8,210,413 | B2 | 7/2012 | Whitman et al. |
| 8,216,250 | B2 | 7/2012 | Orban, III et al. |
| 8,220,468 | B2 | 7/2012 | Cooper et al. |
| 8,256,319 | B2 | 9/2012 | Cooper et al. |
| 8,285,517 | B2 | 10/2012 | Sillman et al. |
| 8,315,720 | B2 | 11/2012 | Mohr et al. |
| 8,335,590 | B2 | 12/2012 | Costa et al. |
| 8,347,757 | B2 | 1/2013 | Duval |
| 8,374,723 | B2 | 2/2013 | Zhao et al. |
| 8,418,073 | B2 | 4/2013 | Mohr et al. |
| 8,419,717 | B2 | 4/2013 | Diolaiti et al. |
| 8,423,182 | B2 | 4/2013 | Robinson et al. |
| 8,452,447 | B2 | 5/2013 | Nixon |
| 8,454,585 | B2 | 6/2013 | Whitman |
| 8,499,992 | B2 | 8/2013 | Whitman et al. |
| 8,508,173 | B2 | 8/2013 | Goldberg et al. |
| 8,528,440 | B2 | 9/2013 | Morley et al. |
| 8,529,582 | B2 | 9/2013 | Devengenzo et al. |
| 8,540,748 | B2 | 9/2013 | Murphy et al. |
| 8,551,116 | B2 | 10/2013 | Julian et al. |
| 8,562,594 | B2 | 10/2013 | Cooper et al. |
| 8,579,176 | B2 | 11/2013 | Smith et al. |
| 8,594,841 | B2 | 11/2013 | Zhao et al. |
| 8,597,182 | B2 | 12/2013 | Stein et al. |
| 8,597,280 | B2 | 12/2013 | Cooper et al. |
| 8,600,551 | B2 | 12/2013 | Itkowitz et al. |
| 8,608,773 | B2 | 12/2013 | Tierney et al. |
| 8,620,473 | B2 | 12/2013 | Diolaiti et al. |
| 8,624,537 | B2 | 1/2014 | Nowlin et al. |
| 8,634,957 | B2 | 1/2014 | Toth et al. |
| 8,638,056 | B2 | 1/2014 | Goldberg et al. |

(56) References Cited

U.S. PATENT DOCUMENTS

| | | |
|---|---|---|
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |

(56) References Cited

U.S. PATENT DOCUMENTS

| | | | |
|---|---|---|---|
| 10,905,506 | B2 | 2/2021 | Itkowitz et al. |
| 10,912,544 | B2 | 2/2021 | Brisson et al. |
| 10,912,619 | B2 | 2/2021 | Jarc et al. |
| 10,918,387 | B2 | 2/2021 | Duque et al. |
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 2002/0099371 | A1 | 7/2002 | Schulze et al. |
| 2002/0177842 | A1 | 11/2002 | Weiss |
| 2003/0125734 | A1 | 7/2003 | Mollenauer |
| 2003/0208186 | A1 | 11/2003 | Moreyra |
| 2006/0022015 | A1 | 2/2006 | Shelton et al. |
| 2006/0025811 | A1 | 2/2006 | Shelton |
| 2007/0233052 | A1 | 10/2007 | Brock |
| 2007/0250113 | A1* | 10/2007 | Hegeman ............. A61B 1/0055 606/207 |
| 2007/0282358 | A1 | 12/2007 | Remiszewski et al. |
| 2008/0015631 | A1 | 1/2008 | Lee et al. |
| 2010/0274265 | A1 | 10/2010 | Wingardner et al. |
| 2010/0292691 | A1 | 11/2010 | Brogna |
| 2011/0118707 | A1 | 5/2011 | Burbank |
| 2011/0118708 | A1 | 5/2011 | Burbank et al. |
| 2011/0118709 | A1 | 5/2011 | Burbank |
| 2011/0118754 | A1 | 5/2011 | Dachs, II et al. |
| 2016/0066982 | A1 | 3/2016 | Marczyk et al. |
| 2019/0117247 | A1 | 4/2019 | Kim et al. |
| 2019/0192245 | A1* | 6/2019 | Abbott ................. B25J 9/1689 |

OTHER PUBLICATIONS

Extended European Search Report issued in corresponding European Application No. 21176129.1 dated Jan. 25, 2022, 14 pages.

\* cited by examiner

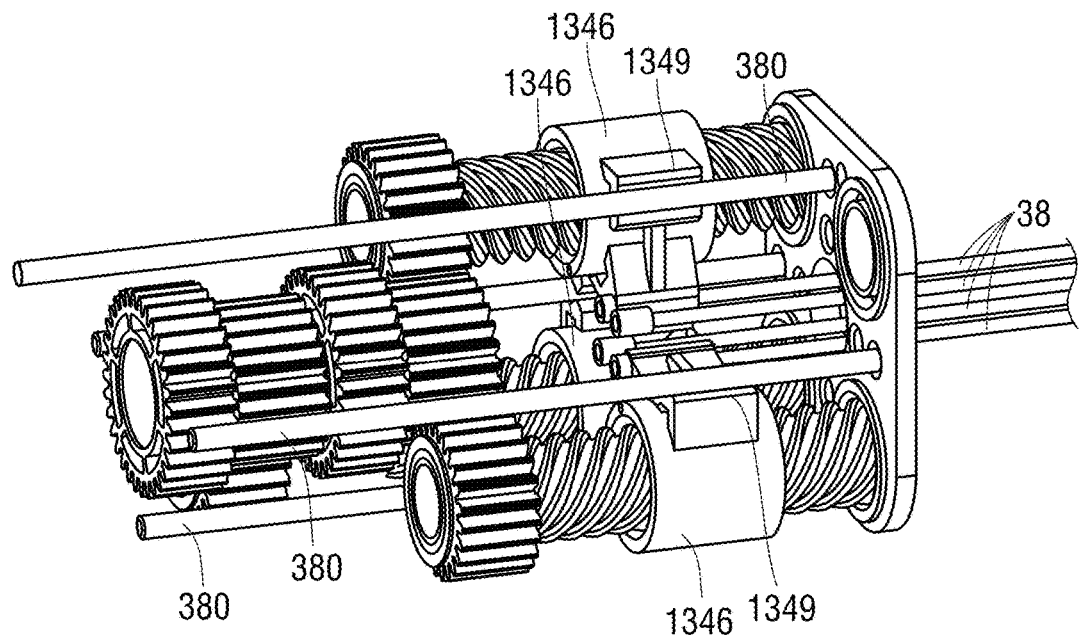
FIG. 5A
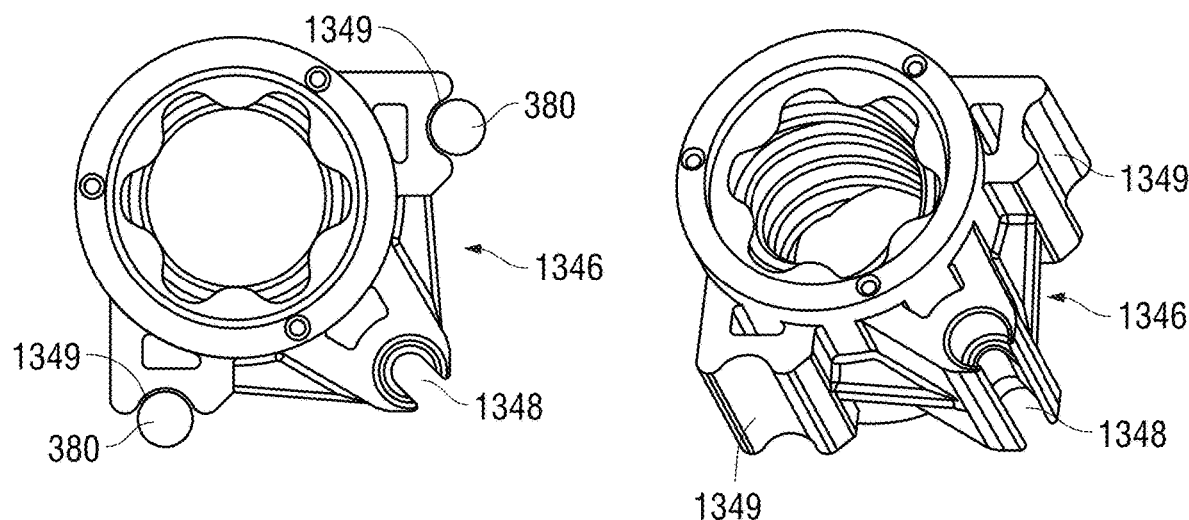
FIG. 5B
FIG. 5C

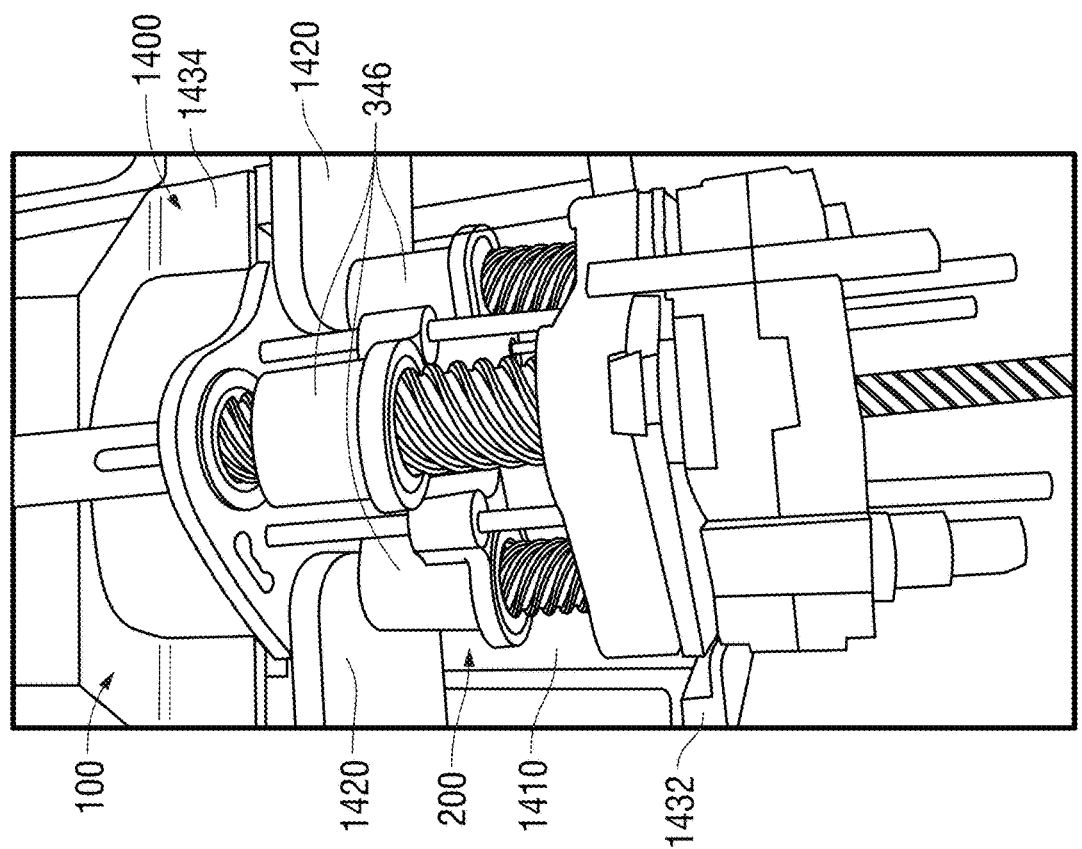
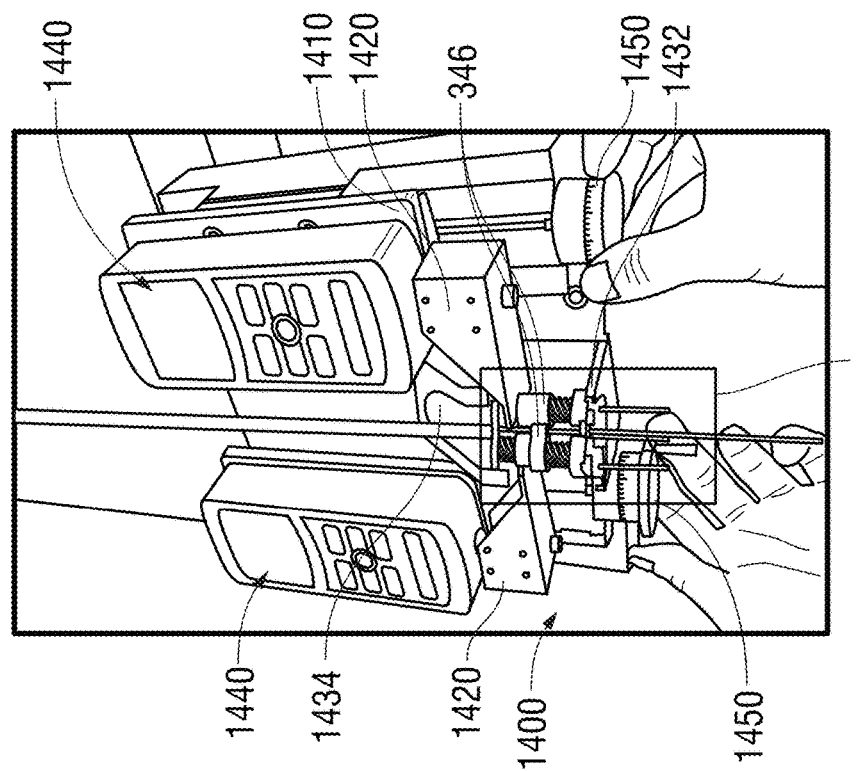
FIG. 6B
FIG. 6A

TENSIONING MECHANISMS AND METHODS FOR ARTICULATING SURGICAL INSTRUMENTS SUCH AS FOR USE IN ROBOTIC SURGICAL SYSTEMS

BACKGROUND

Technical Field

The present disclosure relates to surgical instruments and, more specifically, to articulation mechanisms for surgical instruments such as, for example, for use in robotic surgical systems.

Background of Related Art

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument, e.g., to rotate, articulate, and/or actuate the mounted surgical instrument.

SUMMARY

As used herein, the term "distal" refers to the portion that is being described which is closer to a patient (farther from the surgeon or robot holding the device), while the term "proximal" refers to the portion that is being described which is farther from a patient (closer to the surgeon or robot holding the device). The terms "about," substantially," and the like, as utilized herein, are meant to account for manufacturing, material, environmental, use, and/or measurement tolerances and variations. Further, to the extent consistent, any of the aspects described herein may be used in conjunction with any or all of the other aspects described herein.

Provided in accordance with aspects of the present disclosure is an articulation assembly for a robotic surgical instrument including first and second base plates, a plurality of lead screws extending between the first and second base plates, a collar disposed in threaded engagement about each of the lead screws, and an articulation cable coupled to each of the collars. Each lead screw is rotatable but longitudinally fixed relative to the first and second base plates. Each collar is configured to translate longitudinally along a corresponding one of the lead screws in response to rotation of the corresponding lead screw. Each articulation cable defines or has engaged therewith a threaded shaft. A threaded nipple is disposed in threaded engagement about each of the threaded shafts. Each threaded nipple is engaged with one of the collars to thereby engage each of the articulation cables with a corresponding one of the collars such that longitudinal translation of the corresponding collar pushes or pulls the corresponding articulation cable. Each threaded nipple is configured for further threading or unthreading about the corresponding threaded shaft to vary a pre-tension on the corresponding articulation cable.

In an aspect of the present disclosure, the plurality of lead screws includes four lead screws arranged in a generally square cross-sectional configuration.

In another aspect of the present disclosure, at least one guide dowel extends between the first and second base plates and is coupled with at least one of the collars to inhibit rotation of the at least one collar. In such aspects, each collar may include at least one C-shaped channel wherein each collar is configured to receive a portion of the at least one guide dowel therein to inhibit rotation of each collar.

In still another aspect of the present disclosure, each collar defines a ferrule configured for receipt of the corresponding threaded nipple in engagement therewith.

In yet another aspect of the present disclosure, the articulation assembly further includes a plurality of proximal gear assemblies configured to drive rotation of the plurality of lead screws. In such aspects, a coupling gear may couple two of the proximal gear assemblies such that two of the lead screws are driven by a single input. In aspects, engagement of the coupling gear(s) locks in the pre-tension of articulation cable(s).

A robotic surgical instrument provided in accordance with the present disclosure includes a housing, a shaft extending distally from the housing in fixed longitudinal position relative to the housing, a fixed plate disposed within the housing in fixed longitudinal position relative to the shaft and the housing, and a actuation assembly disposed within the housing. A portion of the actuation assembly includes first and second base plates, a plurality of lead screws extending distally from the first base plate to the second base plate, a collar disposed in threaded engagement about each of the lead screws, and an articulation cable coupled to each of the collars. Each lead screw is rotatable but longitudinally fixed relative to the first and second base plates. Each collar is configured to translate longitudinally along a corresponding one of the lead screws in response to rotation of the corresponding lead screw. Translation of one of the collars tensions or un-tensions a corresponding one of the articulation cables. At least one biasing member is disposed between the second base plate and the fixed plate to bias the portion of the actuation assembly proximally relative to the housing and the shaft, thereby biasing the articulation cables proximally to apply a pre-tension thereto.

The robotic surgical instrument may include any of the aspects detailed above or otherwise herein.

In an aspect of the present disclosure, the at least one biasing member is disposed about the shaft. Alternatively or additionally, the at least one biasing member is centered relative to the plurality of lead screws to substantially equally pre-tension the articulation cables. The at least one biasing member may be a coil compression spring.

Another articulation assembly for a robotic surgical instrument provided in accordance with the present disclosure includes first and second base plates, a plurality of lead screws extending distally from the first base plate to the second base plate, a collar disposed in threaded engagement about each of the lead screws, an articulation cable coupled to each of the collars, and a biasing member disposed about each of the lead screws between the corresponding collar and the second base plate. Each lead screw is rotatable but longitudinally fixed relative to the first and second base plates. Each collar is configured to translate longitudinally along a corresponding one of the lead screws in response to rotation of the corresponding lead screw. Each articulation cable is coupled to one of the collars such that translation of one of the collars tensions or un-tensions a corresponding one of the articulation cables. Each biasing member is configured to bias the corresponding collar proximally relative to the second base plate, thereby biasing the articulation cables proximally to apply a pre-tension thereto.

The articulation assembly may include any of the aspects detailed above or otherwise herein.

In an aspect of the present disclosure, the biasing members are similar to one another such that the articulation cables are substantially equally pre-tensioned.

In another aspect of the present disclosure, the biasing members are coil compression springs.

BRIEF DESCRIPTION OF THE DRAWINGS

Various aspects and features of the present disclosure are described hereinbelow with reference to the drawings wherein like numerals designate identical or corresponding elements in each of the several views.

FIG. 5A is a perspective view of the articulation assembly of FIG. 1A including another configuration of collars;

FIGS. 5B and 5C are front and perspective views, respectively, of one of the collars of FIG. 5A;

FIG. 6A is a perspective view of a tensioning fixture operably supporting the articulation assembly of the surgical instrument of FIG. 1A;

FIG. 6B is an enlarged, perspective view of the area of detail indicated as "6B" in FIG. 6A;

DETAILED DESCRIPTION

Figure 1A:
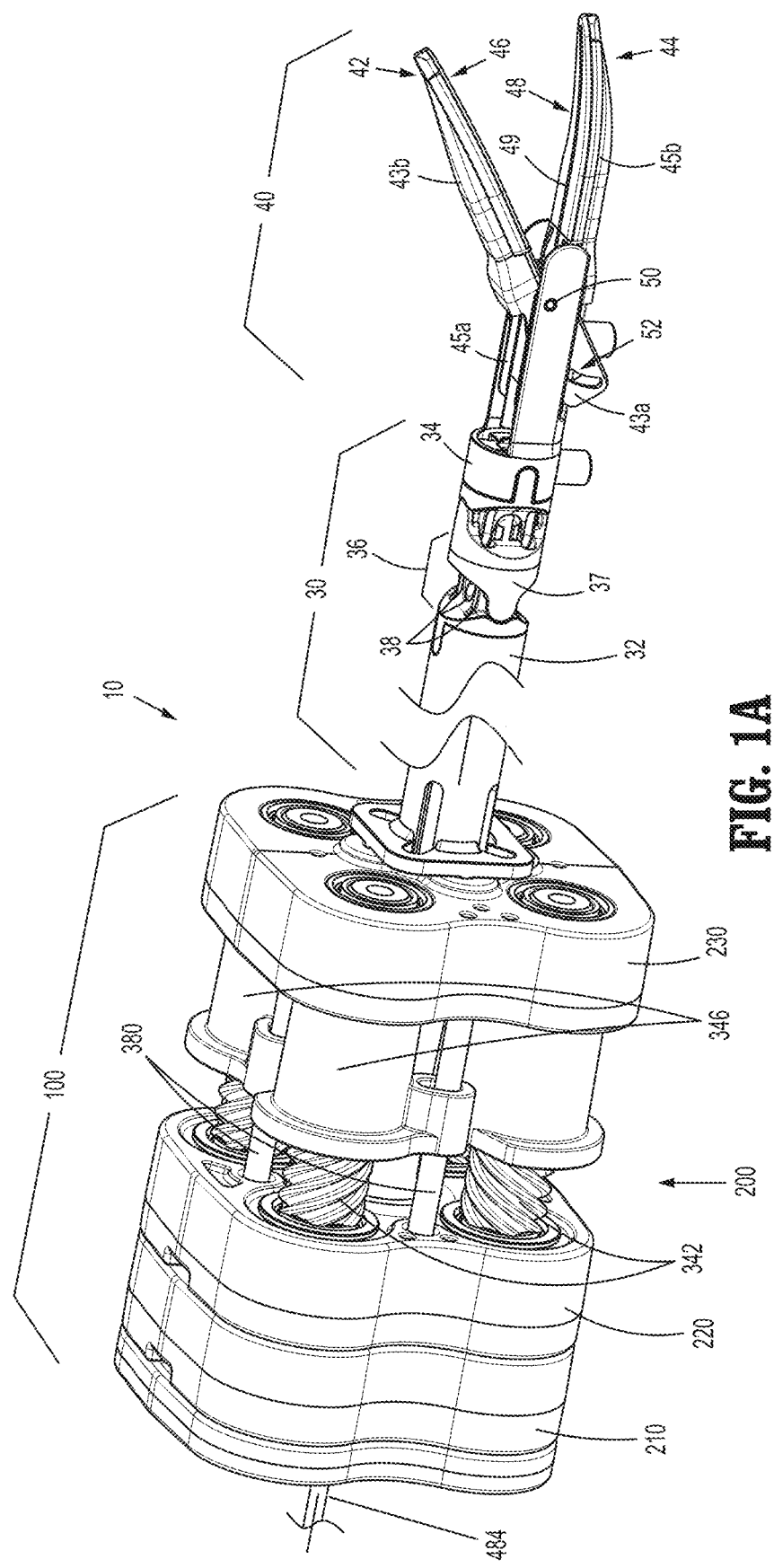
FIG. 1A is a perspective view of an articulation assembly, shaft, and end effector assembly of a surgical instrument provided in accordance with the present disclosure configured for mounting on a robotic arm of a robotic surgical system.
Figure 1B:
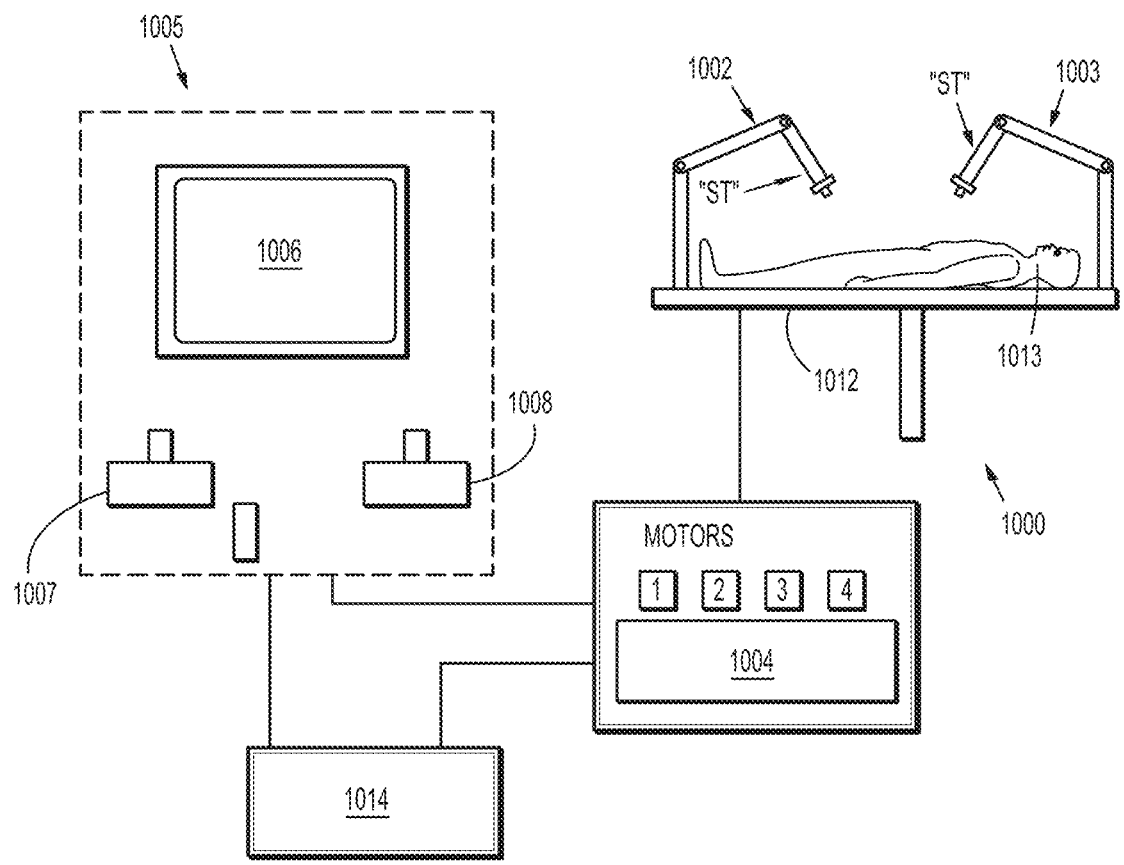
FIG. 1B is a schematic illustration of an exemplary robotic surgical system configured to releasably receive the surgical instrument of FIG. 1A.

Referring to FIG. 1A, a surgical instrument 10 provided in accordance with the present disclosure generally includes a housing (not shown) a shaft 30 extending distally from the housing, an end effector assembly 40 extending distally from shaft 30, and an actuation assembly 100 disposed within the housing and operably associated with end effector assembly 40. Instrument 10 is detailed herein as an articulating electrosurgical forceps configured for use with a robotic surgical system, e.g., robotic surgical system 1000 (FIG. 1B). However, the aspects and features of instrument 10 provided in accordance with the present disclosure, detailed below, are equally applicable for use with other suitable surgical instruments and/or in other suitable surgical systems.

Shaft 30 of instrument 10 includes a proximal segment 32, a distal segment 34, and an articulating section 36 disposed between the proximal and distal segments 32, 34, respectively. Articulating section 36 includes one or more articulating components 37, e.g., links, joints, etc. A plurality of articulation cables 38 (see also FIG. 3), e.g., four (4) articulation cables, or other suitable actuators, extend through articulating section 36. More specifically, articulation cables 38 are operably coupled to distal segment 34 of shaft 30 at the distal ends thereof and extend proximally from distal segment 34 of shaft 30, through articulating section 36 of shaft 30 and proximal segment 32 of shaft 30, and into the housing, wherein articulation cables 38 operably couple with articulation sub-assembly 200 of actuation assembly 100 to enable selective articulation of distal segment 34 (and, thus end effector assembly 40) relative to proximal segment 32 and the housing, e.g., about at least two axes of articulation (yaw and pitch articulation, for example). Articulation cables 38 are arranged to define a generally square configuration, although other suitable configurations are also contemplated.

With respect to articulation of end effector assembly 40 relative to proximal segment 32 of shaft 30, actuation of articulation cables 38 is effected in pairs. More specifically, in order to pitch end effector assembly 40, the upper pair of articulation cables 38 are actuated in a similar manner while the lower pair of articulation cables 38 are actuated in a similar manner relative to one another but an opposite manner relative to the upper pair of articulation cables 38 (see also FIG. 3). With respect to yaw articulation, the right pair of articulation cables 38 are actuated in a similar manner while the left pair of articulation cables 38 are actuated in a similar manner relative to one another but an opposite manner relative to the right pair of articulation cables 38 (see also FIG. 3).

Continuing with reference to FIG. 1A, end effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam pin slidably received within cam slots defined within the proximal flange portion 43a, 45a of at least one of the jaw members 42, 44, respectively, to enable pivoting of jaw member 42 relative to jaw member 44 and distal segment 34 of shaft 30 between a spaced-apart position (e.g., an open position of end effector assembly 40) and an approximated position (e.g., a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 34 of shaft 30.

Longitudinally-extending knife channels 49 (only knife channel 49 of jaw member 44 is illustrated; the knife channel of jaw member 42 is similarly configured) may be defined through tissue-contacting surfaces 46, 48, respectively, of jaw members 42, 44. In such configurations, a knife assembly (not shown) including a knife tube (not shown) extending from the housing through shaft 30 to end effector assembly 40 and a knife blade (not shown) disposed within end effector assembly 40 between jaw members 42, 44 are provided to enable cutting of tissue grasped between tissue-contacting surfaces 46, 48 of jaw members 42, 44, respectively. The knife tube is operably coupled to a knife drive sub-assembly (not shown) of actuation assembly 100 at a proximal end thereof to enable selective actuation to, in turn, reciprocate the knife blade between jaw members 42, 44 to cut tissue grasped between tissue-contacting surfaces 46, 48. Although described herein as sub-assemblies of actuation assembly 100, the articulation sub-assembly 200, the knife drive sub-assembly, and the jaw drive sub-assembly (not shown; detailed below) of actuation assembly 100 are operably independent of one another. That is, actuation assembly 100 generally refers to the various operable sub-assemblies and/or components packaged at least partially within the housing of instrument 10, whether or not they are operably and/or physically linked to one another.

Referring still to FIG. 1A, a drive rod 484 is operably coupled to cam-slot assembly 52 of end effector assembly 40, e.g., engaged with the cam pin thereof, such that longitudinal actuation of drive rod 484 pivots jaw member 42 relative to jaw member 44 between the spaced-apart and approximated positions. More specifically, urging drive rod 484 proximally pivots jaw member 42 relative to jaw member 44 towards the approximated position while urging drive rod 484 distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of drive rod 484 are also contemplated. Drive rod 484 extends proximally from end effector assembly 40 through shaft 30 and into the housing wherein drive rod 484 is operably coupled with a jaw drive sub-assembly (not shown) of actuation assembly 100 to enable selective actuation of end effector assembly 40 to grasp tissue therebetween and apply a closure force within an appropriate jaw closure force range.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, ultrasound, etc., through tissue grasped therebetween for energy-based tissue treatment. Instrument 10 defines a conductive pathway (not shown) through the housing and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator, for supplying energy to tissue-contacting surfaces 46, 48 to treat, e.g., seal, tissue grasped between tissue-contacting surfaces 46, 48.

Actuation assembly 100 is disposed within the housing and, as noted above, includes an articulation sub-assembly 200, a knife drive sub-assembly (not shown), and a jaw drive sub-assembly (not shown). Articulation sub-assembly 200, as detailed below, is operably coupled between first and second rotational inputs, respectively, provided to actuation assembly 100, and articulation cables 38 such that, upon receipt of appropriate inputs into the first and/or second rotational inputs, articulation sub-assembly 200 manipulates articulation cables 38 to articulate end effector assembly 40 in a desired direction, e.g., to pitch and/or yaw end effector assembly 40.

The knife drive sub-assembly is operably coupled to a third rotational input provided to actuation assembly 100 such that, upon receipt of appropriate input into the third rotational input, the knife drive sub-assembly manipulates the knife tube to reciprocate the knife blade between jaw members 42, 44 to cut tissue grasped between tissue-contacting surfaces 46, 48.

The jaw drive sub-assembly is operably coupled between a fourth rotational input provided to actuation assembly 100 and drive rod 484 such that, upon receipt of appropriate input into the fourth rotational input, the jaw drive sub-assembly pivots jaw members 42, 44 between the spaced-apart and approximated positions to grasp tissue therebetween and apply a closure force within an appropriate closure force range.

Actuation assembly 100 is configured to operably interface with a robotic surgical system 1000 (FIG. 1B) when instrument 10 is mounted on robotic surgical system 1000 (FIG. 1B), to enable robotic operation of actuation assembly 100 to provide the above-detailed functionality, e.g., to provide the rotational inputs to actuation assembly 100. However, it is also contemplated that actuation assembly 100 be configured to interface with any other suitable surgical system, e.g., a manual surgical handle, a powered surgical handle, etc. For the purposes herein, robotic surgical system 1000 (FIG. 1B) is generally described.

Turning to FIG. 1B, robotic surgical system 1000 is configured for use in accordance with the present disclosure. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and mounted device which may be, for example, a surgical tool "ST." One or more of the surgical tools "ST" may be instrument 10 (FIG. 1A), thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Figure 2:
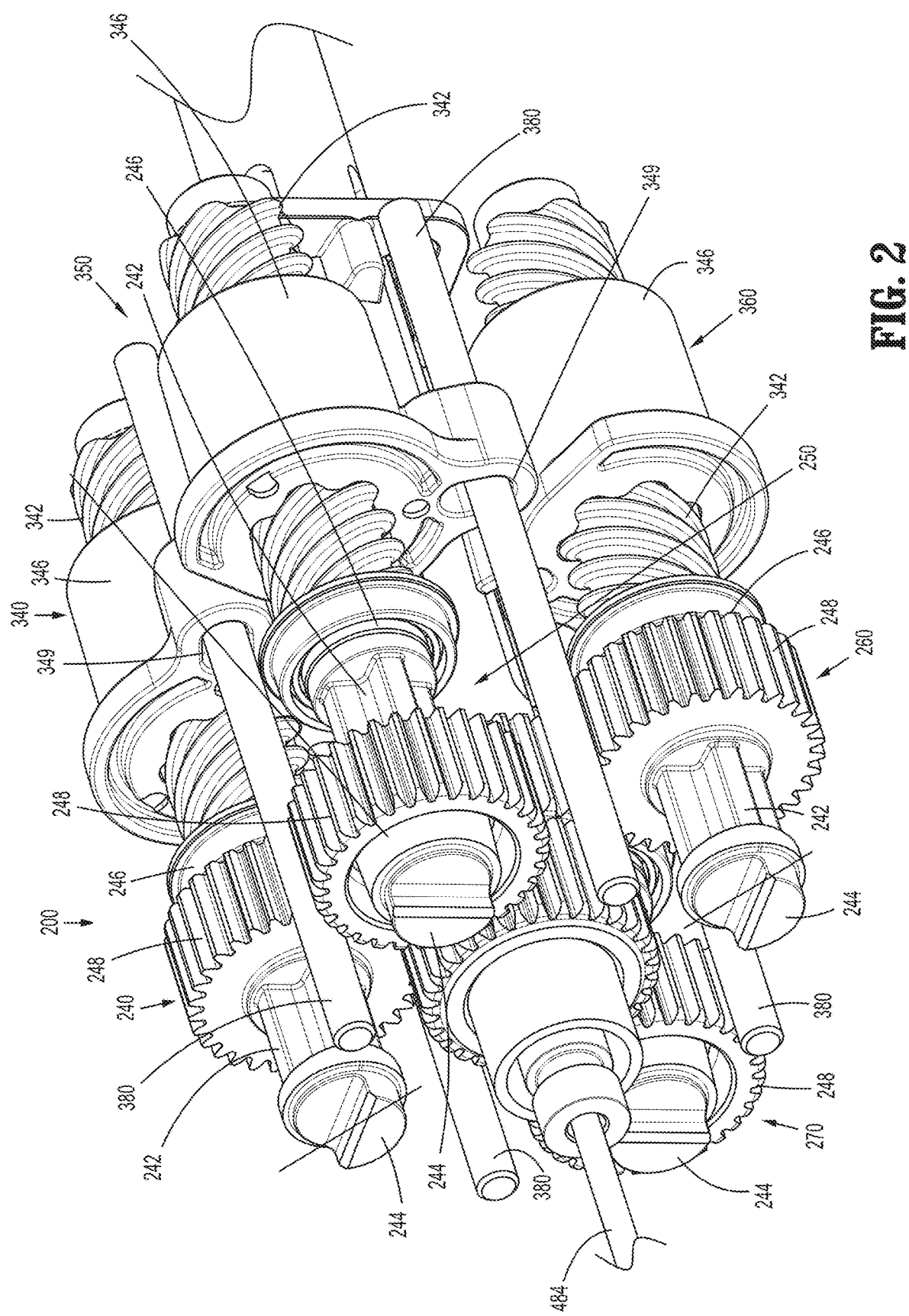
FIG. 2 is a rear, perspective view of the articulation assembly of the surgical instrument of FIG. 1A, with portions removed.
Figure 3:
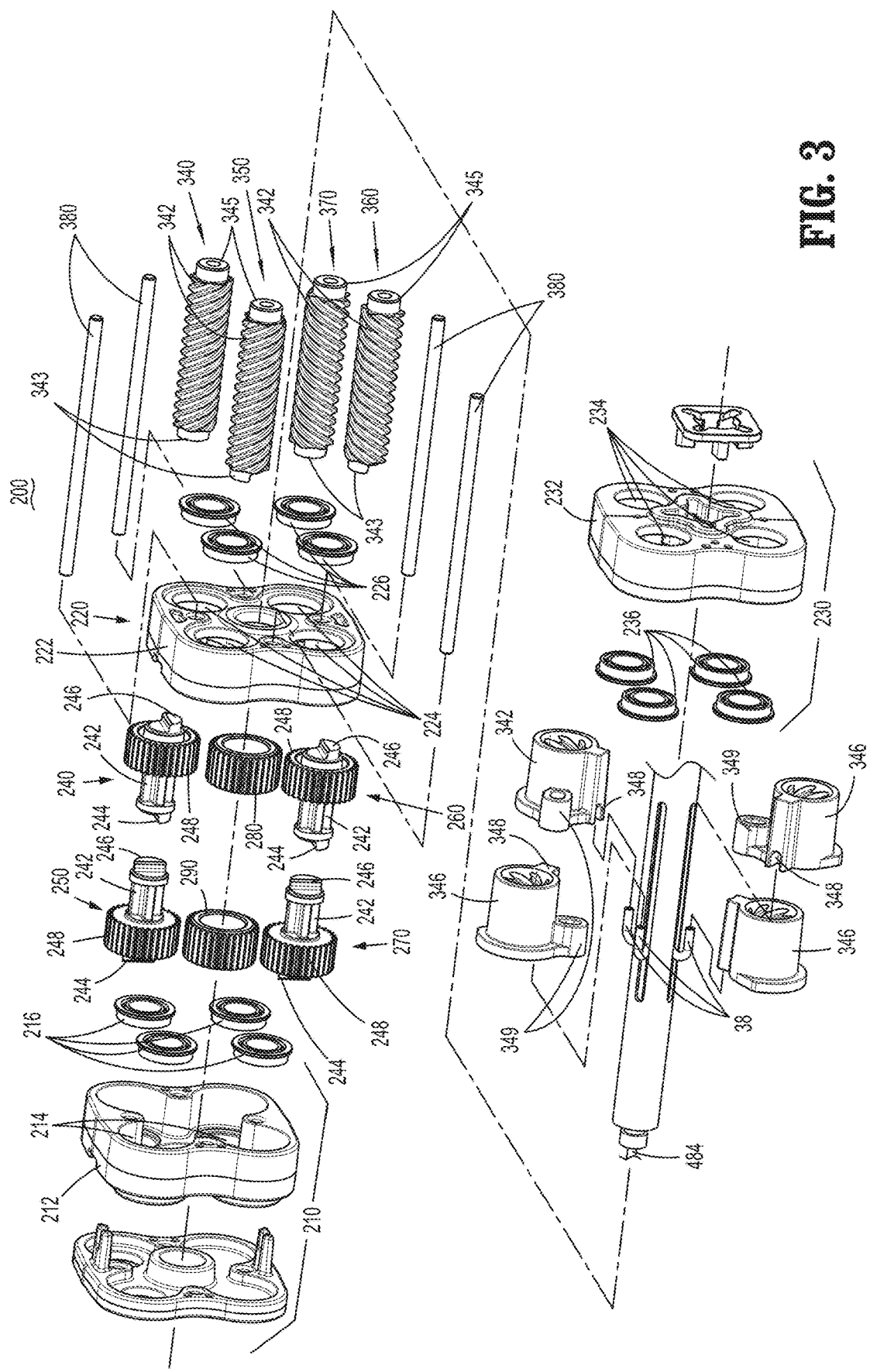
FIG. 3 is an exploded, perspective view of the articulation assembly of the surgical instrument of FIG. 1A.

With reference to FIGS. 1A, 2, and 3, articulation sub-assembly 200 of actuation assembly 100 is shown generally including a proximal base assembly 210, an intermediate base assembly 220, a distal base assembly 230, four proximal gear assemblies 240, 250, 260, 270, two coupling gears 280, 290 four distal gear assemblies configured as lead screw assemblies 340, 350, 360, 370 (although other suitable distal gear assemblies are also contemplated), and four guide dowels 380. As an alternative or in addition to coupling gears 280, 290, belts may be utilized to provide the coupling. Likewise, other gearing components detailed herein may be replaced or supplemented with the use of belts instead of directly meshed gears, without departing from the present disclosure. Further, multiple gears (and/or belts) may be provided in place of single gears (and/or belts) to provide a desired amplification or attenuation effect.

Each of the proximal, intermediate, and distal base assemblies 210, 220, 230, respectively, includes a base plate 212, 222, 232 defining four apertures 214, 224, 234 arranged in a generally square configuration. Bushings 216, 226, 236 are engaged within the apertures 214, 224, 234 of each of proximal, intermediate, and distal base assemblies 210, 220, 230, respectively.

Each proximal gear assembly 240, 250, 260, 270 includes a gear shaft 242 defining an input 244 at a proximal end thereof. However, only two inputs 244 are needed and, indeed, only two are utilized, as detailed below. Thus, in some configurations, only two of the proximal gear assemblies, e.g., proximal gear assemblies 240, 250, include inputs 244 while the other two proximal gear assemblies, e.g., proximal gear assemblies 260, 270, do not. Each proximal gear assembly 240, 250, 260, 270 further includes an output 246 at a distal end thereof. A spur gear 248 is mounted on the respective gear shaft 242 of each proximal gear assembly 240, 250, 260, 270. Proximal gear assemblies 240, 250, 260, 270 are arranged to define a generally square configuration such that the spur gear 248 of each proximal gear assembly 240, 250, 260, 270, includes two adjacent spur gears 248, e.g., a vertically-adjacent spur gear 248 and a horizontally-adjacent spur gear 248, and a diagonally-opposed spur gear 248. One pair of diagonally-opposed spur gears 248, e.g., spur gears 248 of proximal gear assemblies 240, 260, are longitudinally offset relative to the other pair of diagonally-opposed spur gears 248, e.g., spur gears 248 of proximal gear assemblies 250, 270. More specifically, spur gears 248 of proximal gear assemblies 240, 260 are more-distally disposed as compared to spur gears 248 of proximal gear assemblies 250, 270.

The utilized inputs 244 (or inputs 244 provided, where only two are provided), e.g., the inputs 244 of proximal gear assemblies 240, 250, extend proximally into a corresponding bushing 216 disposed within an aperture 214 of base plate 212 of proximal base assembly 210. In this manner, the two inputs 244 are positioned at a proximal end of articulation sub-assembly 200 to receive two rotational inputs for articulation, e.g., from a robotic surgical system 1000 (FIG. 1B). The output 246 of each proximal gear assembly 240, 250, 260, 270 extends distally into a corresponding bushing 226 disposed within an aperture 224 of base plate 222 of intermediate base assembly 220. As detailed below, this enables the output 246 of each proximal gear assembly 240, 250, 260, 270 to provide a rotational output to a corresponding lead screw assembly 340, 350, 360, 370, respectively.

Continuing with reference to FIGS. 1A, 2, and 3, the two coupling gears 280, 290 operably couple the spur gears 248 of each diagonally-opposed pair of spur gears 248. More specifically, the more-distal coupling gear 280 is disposed in meshed engagement with the more-distally disposed spur gears 248 of proximal gear assemblies 240, 260, while the more-proximal coupling gear 290 is disposed in meshed engagement with the more-proximally disposed spur gears 248 of proximal gear assemblies 250, 270.

As a result of the above-detailed configuration, for example, a rotational input provided to input 244 of proximal gear assembly 240 rotates output 246 and spur gear 248 of proximal gear assembly 240 in a first direction to, in turn, rotate coupling gear 280 in a second, opposite direction which, in turn, rotates spur gear 248 and output 246 of proximal gear assembly 260 in the first direction. Further, as another example, a rotational input provided to input 244 of proximal gear assembly 250 rotates output 246 and spur gear 248 of proximal gear assembly 250 in a first direction to, in turn, rotate coupling gear 290 in a second, opposite direction which, in turn, rotates spur gear 248 and output 246 of proximal gear assembly 270 in the first direction. Thus, only two rotational inputs are required to provide a rotational output at the output 246 of each proximal gear assembly 240, 250, 260, 270: one to the input 244 of proximal gear assembly 240 or proximal gear assembly 260, and the other to the input 244 of proximal gear assembly 250 or proximal gear assembly 270. As noted above, only two inputs 244 thus need be provided, e.g., input 244 of proximal gear assembly 240 and input 244 of proximal gear assembly 250.

Each lead screw assembly 340, 350, 360, 370 includes a lead screw 342 defining a proximal input end 343 and a distal dock end 345. Each lead screw assembly 340, 350, 360, 370 further includes a collar 346 disposed in threaded engagement about the corresponding lead screw 342 such that rotation of the lead screw 342 translates the corresponding collar 346 longitudinally therealong. The proximal input end 343 of the lead screw 342 of each lead screw assembly 340, 350, 360, 370 extends proximally into a corresponding bushing 226 disposed within an aperture 224 of base plate 222 of intermediate base assembly 220 wherein the proximal input end 343 is operably coupled with the output 246 of a corresponding proximal gear assembly 240, 250, 260, 270 such that rotation of outputs 246 effect corresponding rotation of lead screws 342. The distal dock end 345 of the lead screw 342 of each lead screw assembly 340, 350, 360, 370 extend distally into and is rotationally seated within a corresponding bushing 236 disposed within an aperture 234 of base plate 232 of distal base assembly 230.

Lead screw assemblies 340, 350, 360, 370, similarly as with proximal gear assemblies 240, 250, 260, 270, are arranged to define a generally square configuration such that the lead screw 342 of each lead screw assembly 340, 350, 360, 370, includes two adjacent lead screws 342, e.g., a vertically-adjacent lead screw 342 and a horizontally-adjacent lead screw 342, and a diagonally-opposed lead screw 342. The lead screws 342 of each diagonally-opposed pair of lead screws 342 define opposite thread-pitch directions. For example, lead screw 342 of lead screw assembly 340 may define a right-handed thread-pitch while the diagonally-opposite lead screw 342 of lead screw assembly 360 defines a left-handed thread-pitch. Similarly, lead screw 342 of lead screw assembly 350 may define a right-handed thread-pitch while the diagonally-opposite lead screw 342 of lead screw assembly 370 defines a left-handed thread-pitch.

As noted above, each collar 346 is operably threadingly engaged about a corresponding lead screw 342 such that rotation of the lead screw 342 translates the corresponding collar 346 longitudinally therealong. Each collar 346 includes a ferrule 348 configured to engage a proximal end portion of one of the articulation cables 38 (see FIG. 3), e.g., via a crimped hook-slot engagement or other suitable engagement (mechanical fastening, adhesion, welding, etc.). Thus, distal translation of a collar 346 slackens the corresponding articulation cable 38 by pushing the corresponding articulation cable 38 in a distal direction, while proximal translation of a collar 346 tensions the corresponding articulation cable 38 by pulling the corresponding articulation cable 38 in a proximal direction.

Figure 4A:
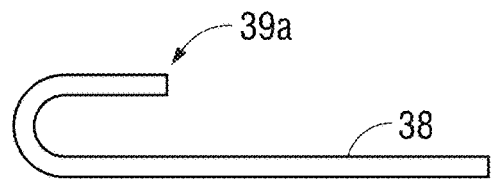
FIGS. 4A through 4G-4 illustrate various proximal end portion configurations of articulation cables to facilitate attachment thereof to a collar.
Figure 4B:
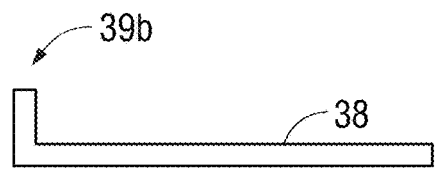
Figure 4C:
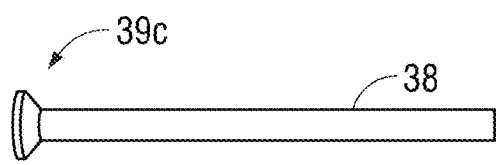
Figure 4D:
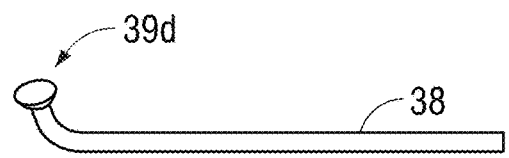
Figures 1, 4E:
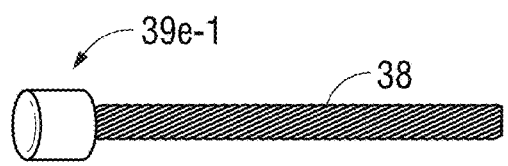
Figures 2, 4E:
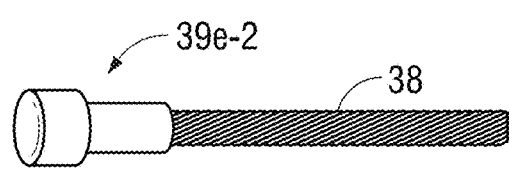
Figures 1, 4F:
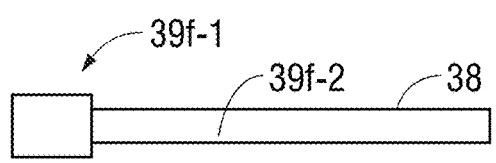
Figures 2, 4F:
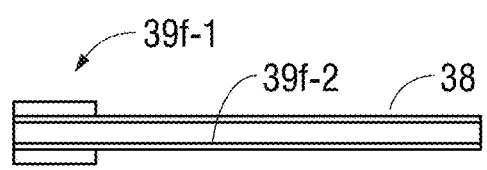

Referring to FIGS. 4A through 4G-4, and with initial reference to FIG. 4A, as noted above, each articulation cable 38 may define or include engaged thereto a J-hook end portion 39a configured for receipt with the ferrule 348 (FIG. 3) of the corresponding collar 346 (FIG. 3). Other suitable end configurations to facilitate engagement within the ferrule 348 (FIG. 3) of the corresponding collar 346 (FIG. 3) are also contemplated. For example: as shown in FIG. 4B, each articulation cable 38 may define or include engaged thereto an L-hook end portion 39b; each articulation cable 38 may define or include engaged thereto a pan head end portion 39c as shown in FIG. 4C; as shown in FIG. 4D, each articulation cable 38 may define or include engaged thereto a spoke end portion 39d; a cap 39e-1 or cap with barrel 39e-2 may be crimped or otherwise engaged about the end portion of each articulation cable 38 as shown in FIGS. 4E-1 and 4E-2, respectively; as shown in FIG. 4F-2 and 4F-2, a donut 39f-1 may be engaged, e.g., welded, about a tube 39f-2 defined by or engaged to the end portion of each articulation cable 38; or, with reference to FIGS. 4G-1 through 4G-4, the end portion of each articulation cable 38 may define or include engaged thereto a rod defining external threading 39g-1 configured for receipt within a threaded bore 39g-3 of a tension nipple 39g-2.

Figures 1, 4G:
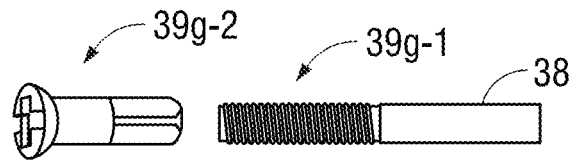
Figures 2, 4G:
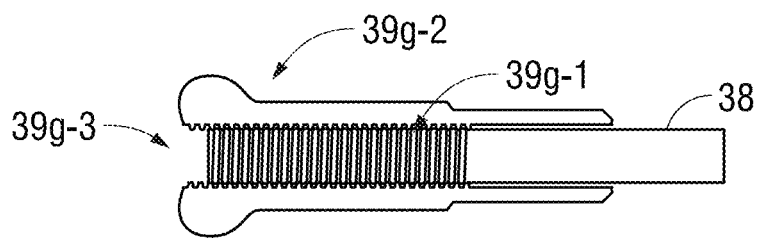
Figures 3, 4G:
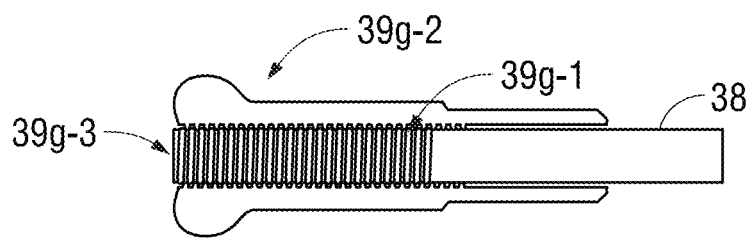
Figures 4, 4G:
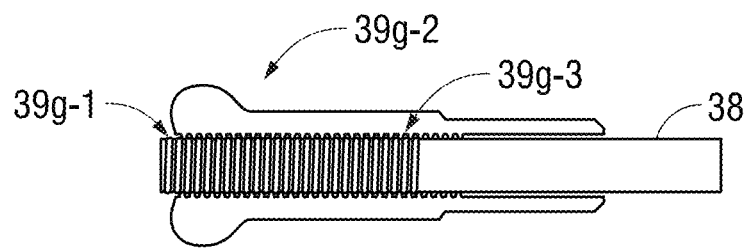

With respect to the configuration illustrated in FIGS. 4G-1 through 4G-4, the threaded engagement between each articulation cable 38 and the corresponding tension nipple 39g-2 not only engages each articulation cable 38 with the ferrule 348 (FIG. 3) of the corresponding collar 346 (FIG. 3), but also enables pre-tensioning of each articulation cable 38 to a desired pre-tension or a pre-tension within a desired pre-tension range. More specifically, as illustrated in FIGS. 4G-2 through 4G-4, the tension nipple 39g-2 may be threaded further onto the external threading 39g-1 and, since the tension nipple 39g-2 is engaged with the ferrule 348 (FIG. 3) of the corresponding collar 346 (FIG. 3), this further threading of the tension nipple 39g-2 pulls the end portion of the corresponding articulation cable 38 proximally relative to the corresponding collar 346 (FIG. 3), thereby increasing the pre-tension on the articulation cable 38. Accordingly, each of the articulation cables 38 may be pre-tensioned in this manner to a desired pre-tension or a pre-tension within a desired pre-tension range. Various other pre-tensioning mechanism and methods are detailed below.

Referring again to FIGS. 1A, 2, and 3, the four guide dowels 380 are engaged and extend between intermediate and distal base assemblies 320, 330, respectively, and are arranged in a generally square configuration. Each guide dowel 380 extends through a sleeve 349 of a collar 346 of a corresponding lead screw assembly 340, 350, 360, 370. Guide dowels 380 guide translation of collars 346 along lead screws 342 and inhibit rotation of collars 346 relative to lead screws 342.

With reference to FIGS. 5A-5C, another configuration of a collar 1346 is shown similar to collars 346 (FIGS. 1A, 2, and 3) except that, rather than each collar defining a sleeve for receipt of a guide dowel 380, each collar 1346 includes a pair of C-shaped channels 1349 disposed at substantially right angles relative to one another. Each C-shaped channel 1349 is configured for receipt of one of the guide dowels 380 partially therein. Thus, each of the four guide dowels 380 is received within a C-shaped channel 1349 of two different collars 1346. While receipt of a dowel 380 within one C-shaped channel 1349 may be insufficient to prevent rotation, e.g., in response to high rotational forces dislodging the dowel 380 from the open mouth of the C-shaped channel 1349, providing a pair of C-shaped channels 1349 disposed at substantially right angles relative to one another with each coupled to a dowel 380 sufficiently inhibits rotation of collars 1346. Collars 1346 may also include open ferrules 1348 for receipt of the end portions of articulation cables 38, rather than fully enclosed ferrules as with collars 346 (FIGS. 1A, 2, and 3).

Turning back to FIGS. 1A, 2, and 3, in order to pitch end effector assembly 40, collars 346 of lead screw assemblies 340, 350 are translated in a similar manner to actuate the upper pair of articulation cables 38 in a similar manner while collars 346 of lead screw assemblies 360, 370 are translated similarly to one another but opposite of the collars 346 of lead screw assemblies 340, 350 such that the lower pair of articulation cables 38 are actuated in a similar manner relative to one another but an opposite manner relative to the upper pair of articulation cables 38. With respect to yaw articulation of end effector assembly 40, collars 346 of lead screw assemblies 340, 370 are translated in a similar manner to actuate the right pair of articulation cables 38 in a similar manner while collars 346 of lead screw assemblies 350, 360 are translated similarly to one another but opposite of the collars 346 of lead screw assemblies 340, 370 such that the left pair of articulation cables 38 are actuated in a similar manner relative to one another but an opposite manner relative to the right pair of articulation cables 38.

Thus, as demonstrated above, the collars 346 of opposing diagonal pairs of collars 346 always move in opposite directions relative to one another to effect articulation, regardless of whether of pitch and/or yaw articulation is desired and regardless of the direction of articulation, e.g., up pitch, down pitch, left yaw, right yaw, or combinations thereof. As also detailed above, a rotational input provided to input 244 of proximal gear assembly 240 or proximal gear assembly 260 provides a similar rotational output at the output 246 of both proximal gear assembly 240 and proximal gear assembly 260 due to the coupling thereof via coupling gear 280 and, thus, lead screw assemblies 340, 360 receive similar inputs from proximal gear assemblies 240, 260, respectively. However, since the thread-pitch of the lead screws 342 of lead screw assemblies 340, 360 are opposite one another, the similar inputs provided thereto effect opposite translation of the collars 346 thereof. Likewise, a rotational input provided to input 244 of proximal gear assembly 250 or proximal gear assembly 270 provides a similar rotational output at both outputs 246 due to the coupling thereof via coupling gear 290 and, thus, lead screw assemblies 350, 370 receive similar inputs from proximal gear assemblies 250, 270, respectively, to, in turn, effect opposite translation of the collars 346 thereof. Thus, by controlling the directions of two rotational inputs (one to the input 244 of proximal gear assembly 240 or proximal gear assembly 260, and the other to the input 244 of proximal gear assembly 250 or proximal gear assembly 270), pitch and/or yaw articulation in any suitable direction may be achieved.

Pre-tensioning articulation cables 38 (FIG. 3) facilitates accurate articulation of end effector assembly 40 (FIG. 1A). As detailed above, tension nipples 39g-2 (FIGS. 4G-1 through 4G-4) may be utilized to pre-tension articulation cables 38 (FIG. 3). Alternatively, with reference to FIGS. 6A and 6B, in conjunction with FIG. 3, a fixture 1400 may be utilized to facilitate pre-tensioning of articulation cables 38 (FIG. 3) prior to engagement of coupling gears 280, 290 (FIG. 3) within articulation sub-assembly 200 of actuation assembly 100. Fixture 1400 includes a base 1410, a pair of tensioning arms 1420 and proximal and distal support plates 1432, 1434. Fixture 1400 may further include or enable operable coupling with one or more force gauges 1440 to provide feedback, e.g., input load data, as to the pre-tension on articulation cables 38. Where multiple force gauges 1440 are provided, each force gauge 1440 may provide independent feedback as to the pre-tension on one or more articulation cables 38. For example, as illustrated in FIG. 6A, two force gauges 1440 may be included, each providing independent feedback from one of the tensioning arms 1420.

Proximal and distal support plates 1432, 1434 are configured to retain articulation sub-assembly 200 of actuation assembly 100 in substantially fixed position although, in some configurations, only proximal support plate 1432 is provided. Tensioning arms 1420 are configured to engage an opposing diagonal pair of collars 346. Tensioning arms 1420 are coupled to one or more drives 1450, e.g., gear sets, motors, pulleys, slides, etc., independently or commonly, to enable selective translation of tensioning arms 1420 proximally, e.g., manually or automatically. Proximal movement of tensioning arms 1420, in turn, moves the opposing diagonal pair of collars 346 proximally to tension the corresponding articulation cables 38 to a desired pre-tension or pre-tension within a desired pre-tension range. The pre-tensions are verified using the outputs of the force gauges 1440.

The above-detailed pre-tensioning may first be performed, for example, by inserting articulation sub-assembly 200 of actuation assembly 100 into fixture 1400 such that the collars 346 associated with lead screw assemblies 340, 360 (FIG. 3) are engaged with tensioning arms 1420. In this manner, the articulation cables 38 associated with lead screw assemblies 340, 360 are pre-tensioned. Once this pre-tension has been achieved, coupling gear 280 (FIG. 3) is inserted into meshed engagement with spur gears 248 (FIG. 3) of proximal gear assemblies 240, 260 (FIG. 3) such that the articulation cables 38 associated with lead screw assemblies 340, 360 are maintained in pre-tension. Alternatively, lead screw assemblies 340, 360 may otherwise be secured to maintain the pre-tension.

Thereafter, articulation sub-assembly 200 of actuation assembly 100 may be removed, rotated, and re-inserted into fixture 1400 such that the collars 346 associated with lead screw assemblies 350, 370 (FIG. 3) are engaged with tensioning arms 1420. In this manner, the articulation cables 38 associated with lead screw assemblies 350, 370 are pre-tensioned. Once this pre-tension has been achieved, coupling gear 290 (FIG. 3) is inserted into meshed engagement with spur gears 248 (FIG. 3) of proximal gear assemblies 250, 270 (FIG. 3) such that the articulation cables 38 associated with lead screw assemblies 350, 370 are maintained in pre-tension. Alternatively, lead screw assemblies 350, 370 may otherwise be secured to maintain the pre-tension. It is also contemplated that the above order be reversed or that other suitable pairs of leas screw assemblies, 340-370 be pre-tensioned in the above-detailed manner.

Figure 7A:
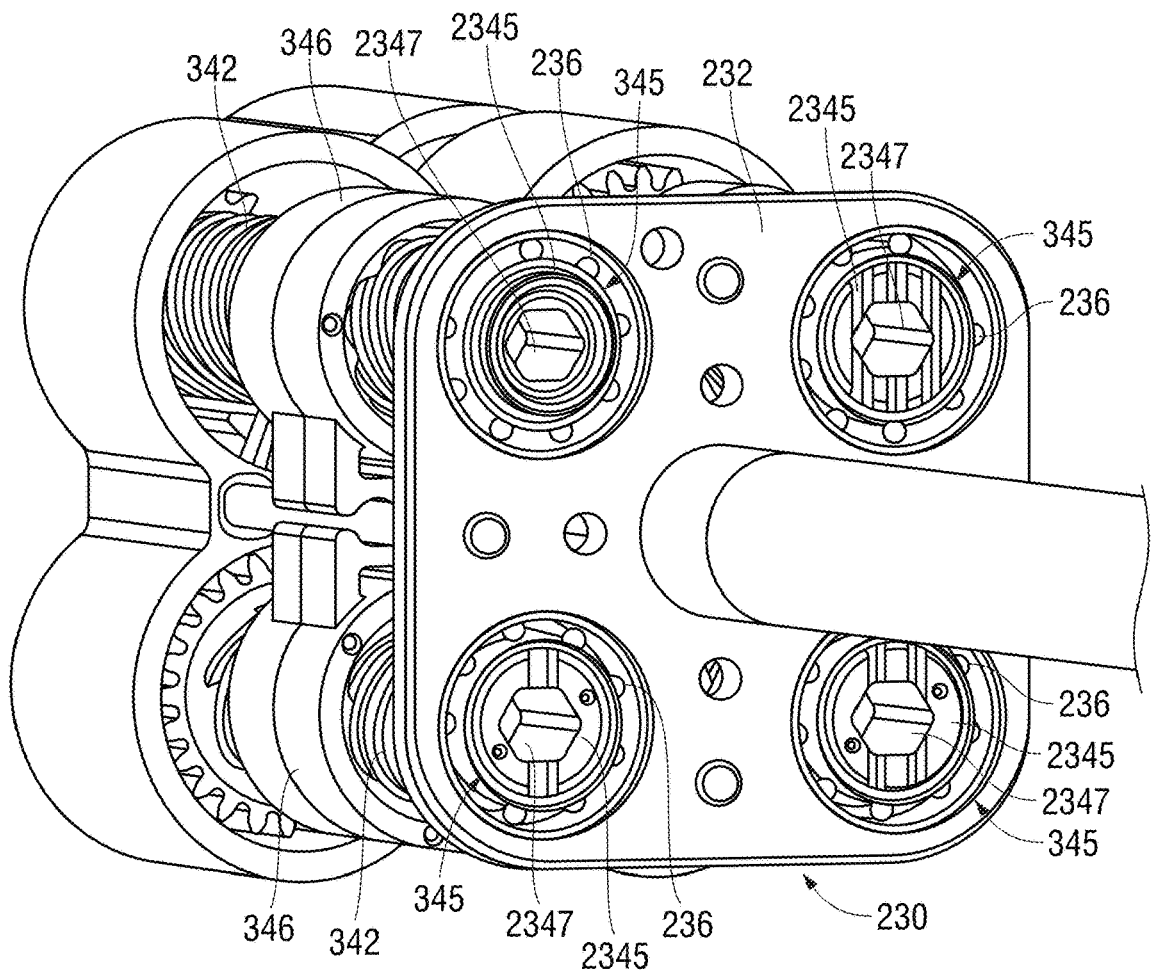
FIG. 7A is a perspective view of the articulation assembly of FIG. 1A including another configurations of lead screws.
Figure 7B:
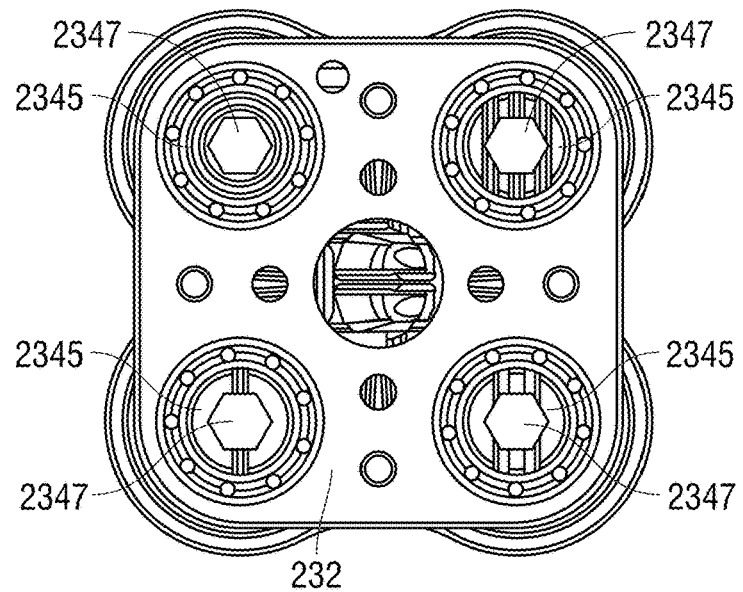
FIG. 7B is a front view of the articulation assembly of FIG. 1A including the lead screws of FIG. 7A.

Referring to FIGS. 7A-9, in conjunction with FIG. 3, and initially to FIGS. 3, 7A, and 7B, in order to facilitate pre-tensioning of articulation cables 38 (FIG. 3) lead screws 342 (individually, in pairs, or collectively) may be rotated to drive collars 346 proximally, thereby tensioning articulation cables 38. This may be accomplished, for example via defining engagable patterns 2347 as recesses within end faces 2345 of distal dock ends 345 of lead screws 342. As noted above, distal base assembly 230 includes base plate 232 defining four apertures 234 (FIG. 3) arranged in a generally square configuration. Bushings 236, e.g., ball bearings, are engaged within the apertures 234 defined within base plate 232 and the distal dock ends 345 of the lead screws 342 are engaged within bushings 236 thus rotationally seating lead screws 342 within base plate 232 of distal base assembly 230. As illustrated in FIGS. 7A and 7B, the engagable patterns 2347 defined within end faces 2345 may be similar to one another and may be, for example, hexagonal recesses, although other geometric or other suitable engagable patterns 2347 are also contemplated. The hexagonal recesses are configured to receive a hexagonal driver or other suitable driver (not shown) to enable rotational driving of lead screws 342. Lead screws 342, more specifically, are driven to rotate to thereby translate drive collars 346 proximally therealong. This proximal translation of drive collars 346 pre-tensions the articulation cables 38.

Pre-tensioning of the articulation cables 38 associated with a first pair of diagonally-opposed lead screws 342, e.g., the lead screws of lead screw assemblies 340, 360 (FIG. 3), may be accomplished prior to engagement of coupling gear 280 (FIG. 3) therebetween. Once the pre-tension has been achieved, coupling gear 280 is inserted into position such that the articulation cables 38 associated with lead screw assemblies 340, 360 are maintained in pre-tension. Thereafter or therebefore, the articulation cables 38 associated with the other pair of diagonally-opposed lead screws 342, e.g., the lead screws 342 of lead screw assemblies 350, 370 (FIG. 3), are pre-tensioned in a similar manner and coupling gear 290 (FIG. 3) is engaged therebetween to maintained the pre-tension.

Figure 8:
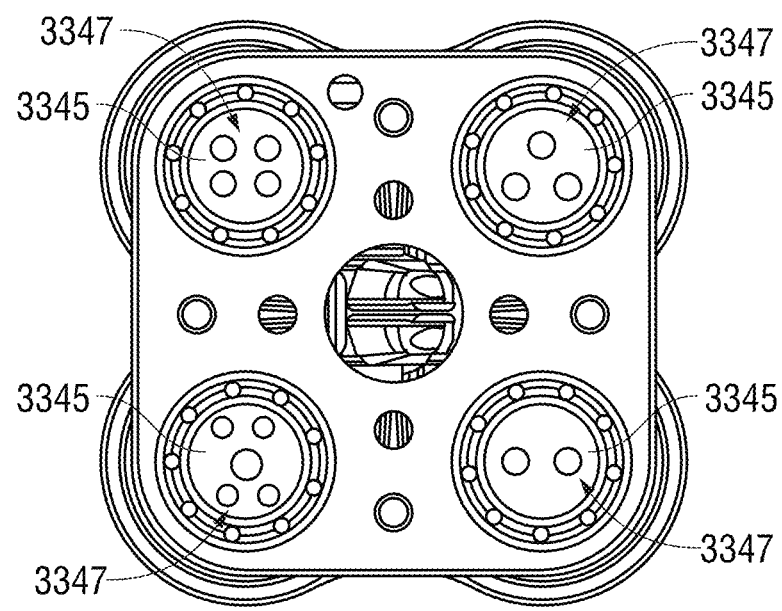
FIGS. 8 and 9 are front views of the articulation assembly of FIG. 1A including other configurations of lead screws.

With reference to FIG. 8, as opposed to geometric shapes and/or similar engagable patterns, other configurations of engagable patterns 3347 may be defined as recesses within the end faces 3345 of lead screws 342 (FIG. 7A). For example, engagable patterns 3347 may include similar or different aperture configurations configured to receive multi-pin drivers (not shown) to enable rotational driving of the lead screws 342 (FIG. 7A), e.g., two-pin, three-pin, four-pin, and five-pin drivers configured for engagement within the two-aperture, three-aperture, four-aperture, and five-aperture engagable patterns 3347, respectively. By providing engagable patterns 3347 for the different lead screws 342 (FIG. 7A), identification of the lead screws 342 (FIG. 7A) and, thus, their appropriate position in the articulation sub-assembly 200 of actuation assembly 100 (see FIG. 3) during assembly can be readily achieved. As an alternative to requiring different drivers, it is contemplated that a universal driver (not shown) configured to engage each of the engagable patterns 3347 (or any of the other engagable patterns detailed herein) may be utilized.

Figure 9:
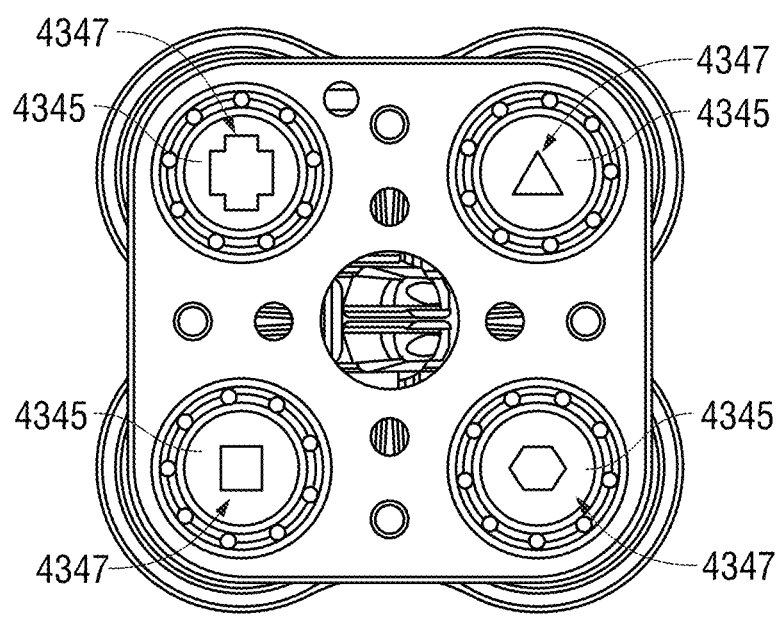

FIG. 9 illustrates other configurations of engagable patterns 4347 defined as recesses within the end faces 4345 of lead screws 342 (FIG. 7A), e.g., various different geometric patterns such as a square (or other quadrilateral), hexagon, triangle, and/or cross.

Figure 10:
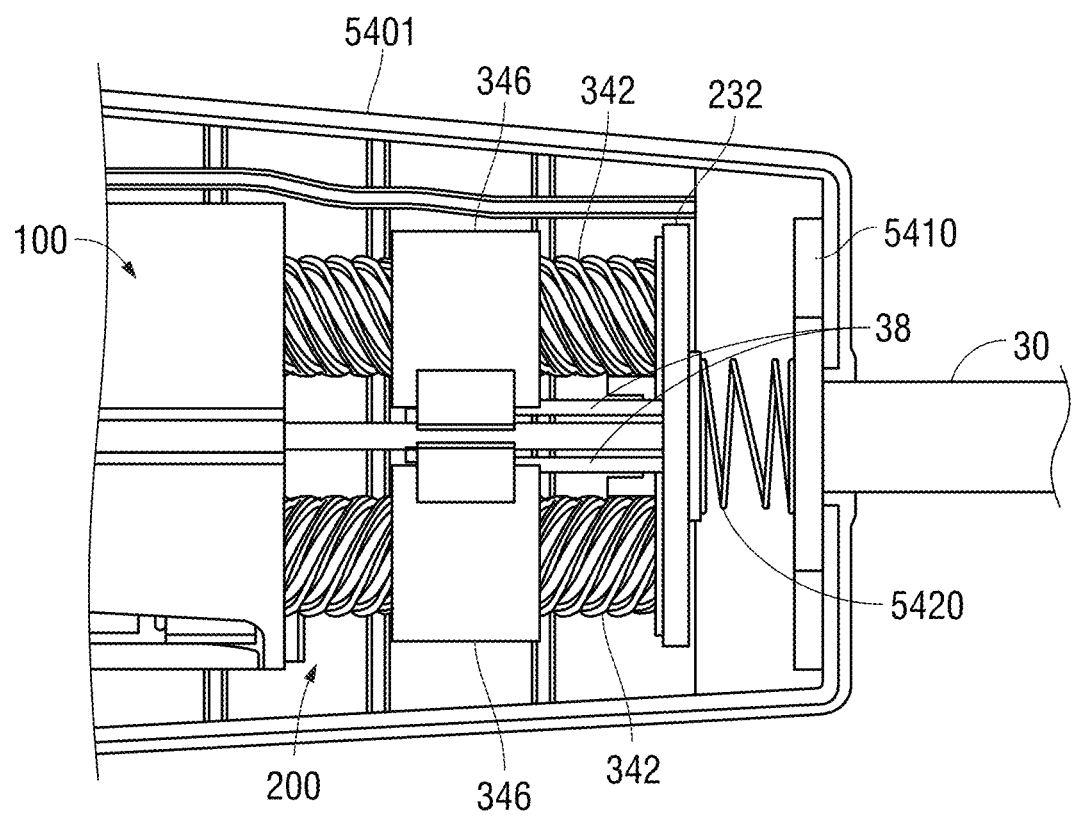
FIG. 10 is a side view, with a portion of a housing removed, of the articulation assembly of FIG. 1A including a fixed plate and biasing member operably coupled thereto.

Turning to FIG. 10, one or more springs may be utilized to pre-tension articulation cables 38. More specifically, rather than longitudinally securing at least base plate 232 and lead screws 342 of articulation sub-assembly 200 of actuation assembly 100 within and relative to the outer housing 5401 that houses actuation assembly 100, at least a portion of articulation sub-assembly 200 of actuation assembly 100, e.g., at least base plate 232 and lead screws 342, may float, allowing longitudinal translation within and relative to outer housing 5401 and, thus, relative to shaft 30 and the distal end portions of articulation cables 38. In some configurations, a fixed distal plate 5410 is engaged, in longitudinally fixed position about a proximal end portion of shaft 30 and/or to housing 5401. Fixed distal plate 5410 is distally-spaced from base plate 232 of articulation sub-assembly 200 of actuation assembly 100. A biasing member 5420, e.g., a compression coil spring, is disposed between fixed distal plate 5410 and base plate 232, and may be disposed about shaft 30. Biasing member 5420 biases base plate 232 proximally relative to fixed distal plate 5410 and, thus, relative to housing 5401, shaft 30, and articulation cables 38. In this manner, the at least a portion of (or the entirety of) articulation sub-assembly 200 of actuation assembly 100 floats within housing 5410 whereby biasing member 5420 acts to apply and maintain a desired pre-tension or a pre-tension within a desired pre-tension range on articulation cables 38 by biasing base plate 232, lead screws 342, and collars 346 (and, thus, the proximal end portions of articulation cables 38) proximally.

The centered location of biasing member 5420 relative to lead screws 342 and, thus, relative to articulation cables 38 provides a substantially equally-distributed proximal force on base plate 232 such that a substantially equal pre-tension on each of the articulation cables 38 is achieved. As an alternative to a single, centered biasing member 5420, other suitable arrangements of one or more biasing members disposed between fixed distal plate 5410 and base plate 232 may be provided that enable equal pre-tension on each of the articulation cables 38.

Figure 11A:
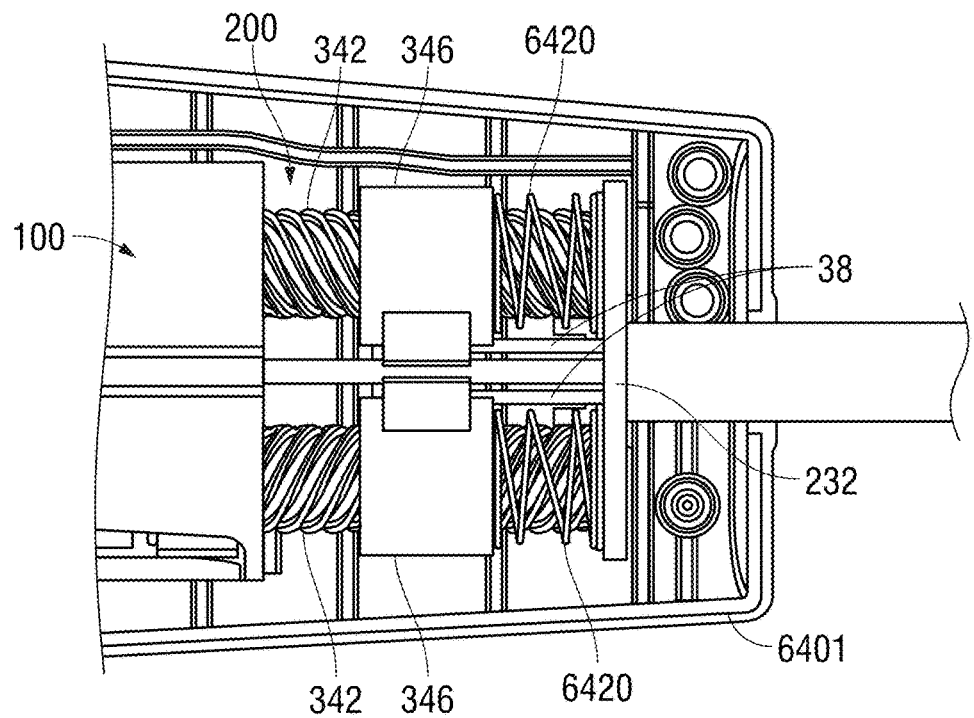
FIGS. 11A and 11B are side views, with portions of housings removed, of the articulation assembly of FIG. 1A including plurality of biasing members operably coupled thereto and disposed in initial and articulated conditions, respectively.
Figure 11B:
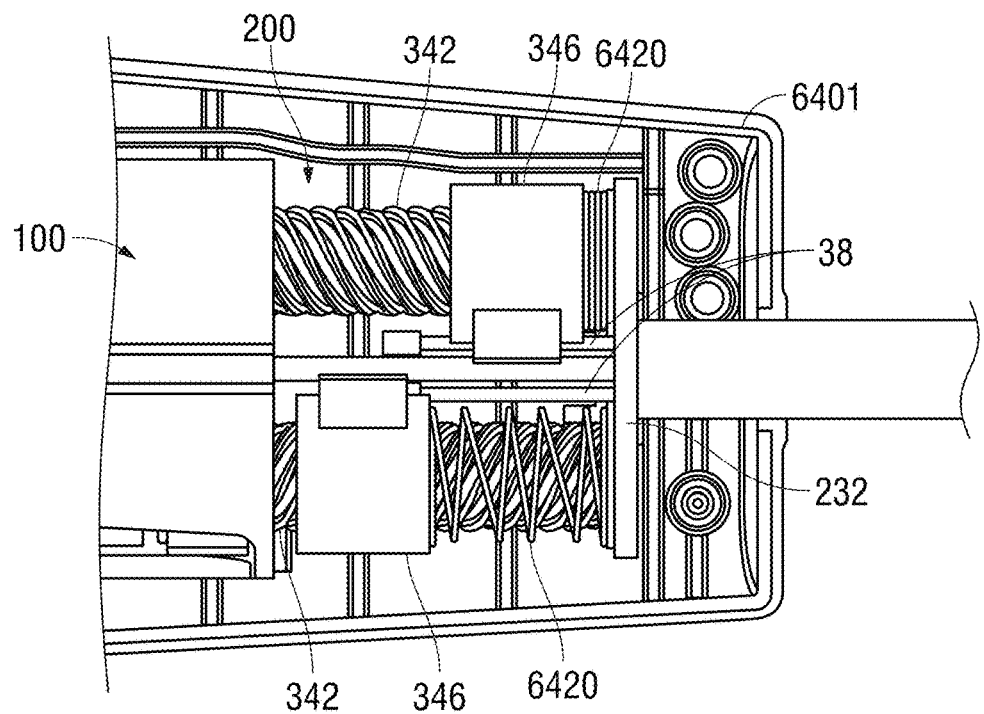

Referring to FIGS. 11A and 11B, in another configuration, base plate 232 and lead screws 342 are longitudinally-fixed within housing 6401 (which houses actuation assembly 100) and a biasing member 6420, e.g., a coil compression spring, is disposed about each lead screw 342 between the collar 346 thereof and base plate 232. Biasing members 6420 thus act to bias collars 346 proximally to pre-tension articulation cables 38. Biasing members 6420 are similarly configured and position such that a substantially equal proximal force is provided on each collar 346, thereby applying a substantially equal pre-tension on each of the articulation cables 38. As can be appreciated due to the positioning of biasing members 6420, as a lead screw 342 is driven to advance the corresponding collar 346 distally, the biasing member 6420 disposed between that collar 346 and base plate 232 is compressed thereby increasing the requisite driving force, while, on the other hand, as a lead screw 342 is driven to retract the corresponding collar 346 proximally, the biasing member 6420 disposed between that collar 346 and base plate 232 is allowed to extend further, thereby decreasing the requisite driving force. Similarly as detailed above, coupling gears 280, 290 (FIG. 3), once installed, serve to lock the pre-tension on articulation cables 38 applied by biasing member 6420.

Figure 12B:
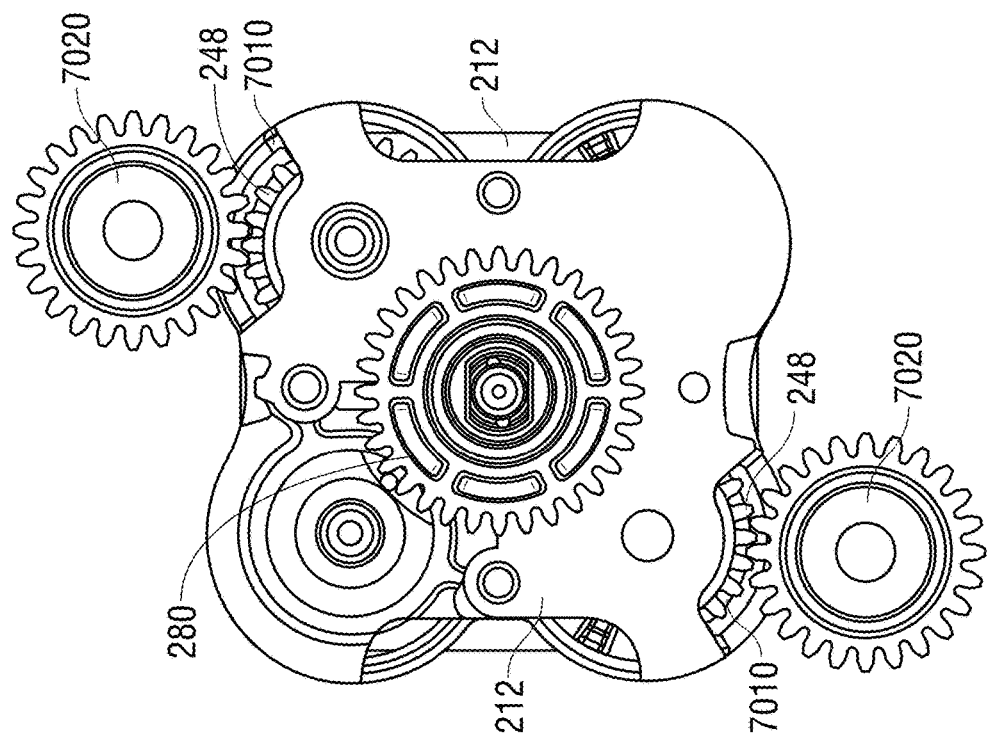
FIG. 12A and 12B are rear views of the articulation assembly of FIG. 1A at various stages of assembly including driver gears coupled thereto.
Figure 12A:
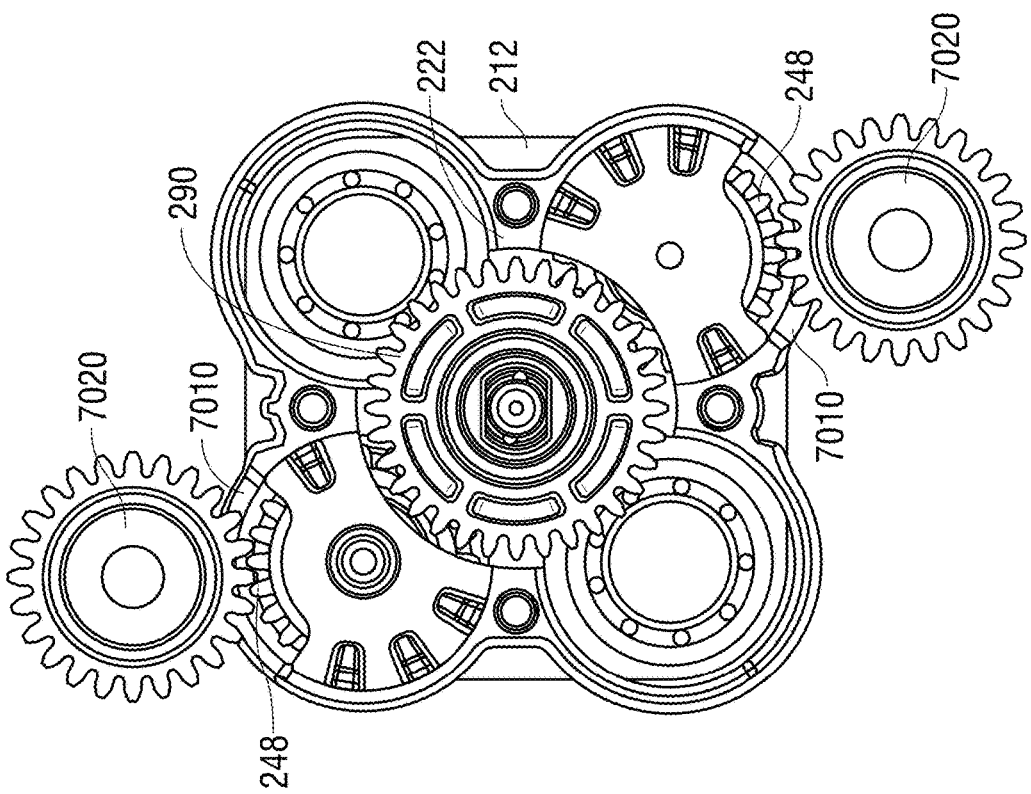

With reference to FIGS. 12A and 12B, in conjunction with FIGS. 2 and 3, still another configuration that facilitates pre-tensioning of the articulation cables 38 (FIG. 3) in accordance with the present disclosure is provided. As detailed above, a spur gear 248 is fixedly mounted on each gear shaft 242 (FIGS. 2 and 3) and each gear shaft 242 is engaged, in fixed rotational orientation, with a corresponding lead screw 342 (FIGS. 2 and 3). Thus, rotation of a spur gear 248 drives rotation of a corresponding lead screw 342 to thereby translate the corresponding collar 346 (FIGS. 2 and 3) therealong to further tension or un-tension the corresponding articulation cable 38. In some configurations, base plate 212 and/or base plate 222 define transverse cut-outs 7010 exposing portions of the outer gear circumferences of spur gears 248. More specifically, cut-outs 7010 sufficiently expose spur gears 248 to enable driver gears 7020 to be disposed in meshed engagement therewith and, upon rotation of the drive gears 7020, to drive rotation of the spur gears 248.

The above-detailed configuration enables, prior to engagement of coupling gear 280 between the spur gears 248 of a first pair of diagonally-opposed lead screws 342, those spur gears 248 to be engaged by drive gear(s) 7020 and driven to rotate to thereby rotate the corresponding lead screws 342 to translate collars 346 proximally to pre-tension the corresponding articulation cables 38. Once the pre-tension has been achieved, coupling gear 280 is inserted into position such that the articulation cables 38 associated with those driven lead screws 342 are maintained in pre-tension. The articulation cables 38 associated with the other pair of diagonally-opposed lead screws 342 are pre-tensioned in a similar manner and coupling gear 290 is engaged therebetween to maintained the pre-tension.

Figure 13A:
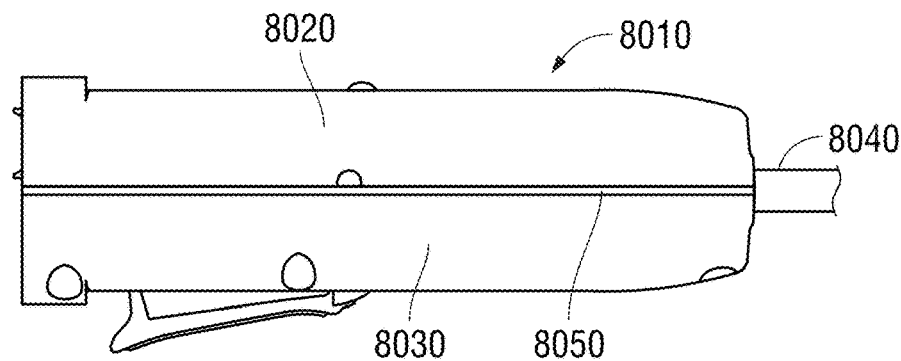
FIG. 13A is a side view of a housing configured for use with the surgical instrument of FIG. 1A or any other suitable robotic surgical instrument.
Figure 13B:
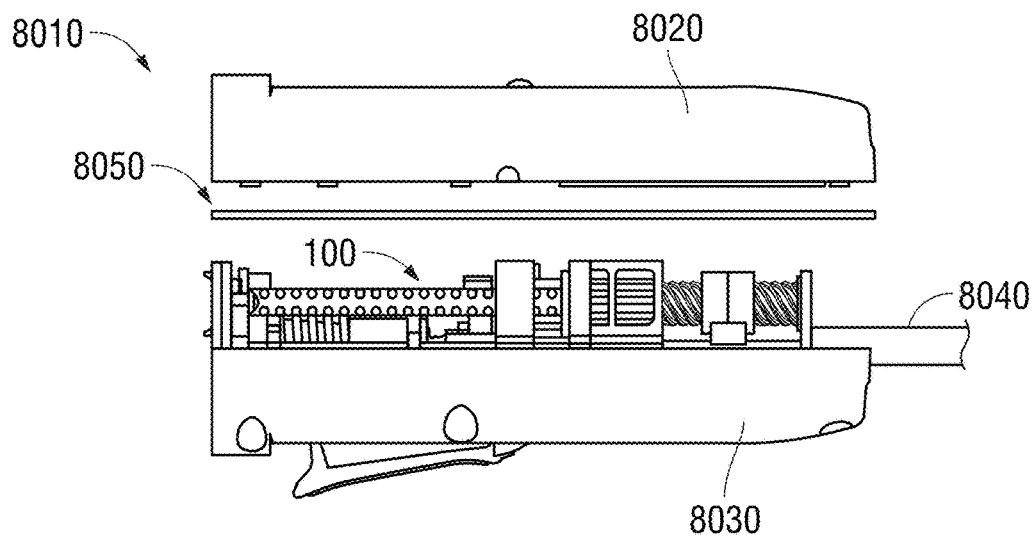
FIG. 13B is an exploded view of the housing of FIG. 13A including a actuation assembly disposed therein.
Figure 13C:
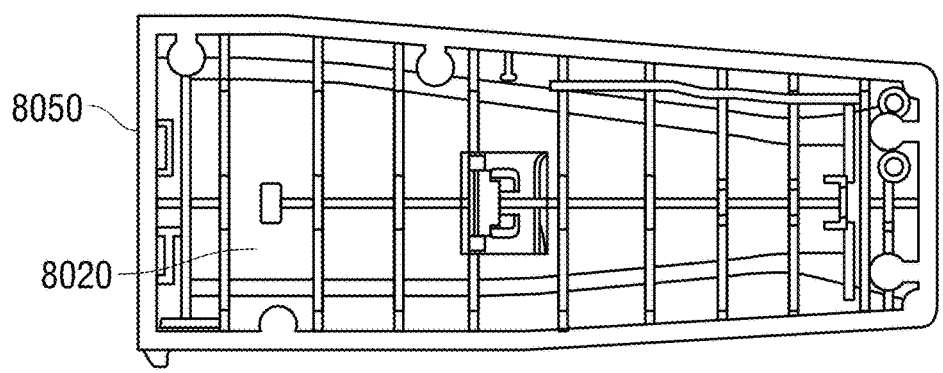
FIG. 13C is an interior view of one of the housing components of the housing of FIG. 13A.

Turning to FIGS. 13A-13C, a housing 8010 configured for use with surgical instrument 10 or other suitable robotic surgical instrument is shown. Housing 8010 is formed form first and second housing components 8020, 8030 secured to one another about their perimeters to seal off the interior volume thereof that houses actuation assembly 100 therein. Housing 8010 is further configured to seal about shaft 8040 which extends distally therefrom.

In order to seal housing 8010, a foam tape 8050 is disposed on the perimeter mating surface of one of the housing components 8020, 8030 and the housing components 8020, 8030 are pressed together to bond and seal the housing 8010. The foam tape 8050 may be double-sided to includes acrylic adhesive or other suitable adhesive on both sides of a conformable foam base to enable adhesion and sealing with housing components 8020, 8030. This configuration provides high-strength, durable permanent bonding that establishes a permanent seal against moisture and fluids such as blood, saline, water etc. Further, this configuration eliminates the need for more expensive and/or labor-intensive methods such as press-fitting, screws, snaps, ultrasonic welding, etc.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. An articulation assembly for a robotic surgical instrument, comprising:
    first and second base plates;
    a plurality of lead screws extending between the first and second base plates, each lead screw rotatable but longitudinally fixed relative to the first and second base plates;
    a collar disposed in threaded engagement about each of the lead screws, each collar configured to translate longitudinally along a corresponding one of the lead screws in response to rotation of the corresponding lead screw;

an articulation cable coupled to each of the collars, each articulation cable defining or having engaged therewith a threaded shaft; and a threaded nipple disposed in threaded engagement about each of the threaded shafts, each threaded nipple engaged with one of the collars to thereby engage each of the articulation cables with a corresponding one of the collars such that longitudinal translation of the corresponding collar pushes or pulls the corresponding articulation cable, wherein each threaded nipple is configured for further threading or unthreading about the corresponding threaded shaft to vary a pre-tension on the corresponding articulation cable, and wherein each collar defines a ferrule configured for receipt of the corresponding threaded nipple in engagement therewith.

2. The articulation assembly according to claim 1, wherein the plurality of lead screws includes four lead screws arranged in a generally square cross-sectional configuration.

3. The articulation assembly according to claim 1, further comprising at least one guide dowel extending between the first and second base plates and coupled with at least one of the collars to inhibit rotation of the at least one collar.

4. The articulation assembly according to claim 3, wherein each collar includes at least one C-shaped channel, the at least one C-shaped channel of each collar configured to receive a portion of the at least one guide dowel therein to inhibit rotation of each collar.

5. The articulation assembly according to claim 1, further comprising a plurality of proximal gear assemblies configured to drive rotation of the plurality of lead screws.

6. The articulation assembly according to claim 5, wherein a coupling gear couples two of the proximal gear assemblies such that two of the lead screws are driven by a single input, the coupling gear locking the pre-tension on the articulation cables corresponding to the two lead screws.

7. A robotic surgical instrument, comprising:
a housing;
a shaft extending distally from the housing, the shaft longitudinally secured to the housing thereby maintaining the shaft in fixed longitudinal position relative to the housing;
a fixed plate disposed within the housing, the fixed plate longitudinally secured to the housing thereby maintaining the fixed plate in fixed longitudinal position relative to the shaft and the housing;
an actuation assembly disposed within the housing, a portion of the actuation assembly including:
first and second base plates;
a plurality of lead screws extending distally from the first base plate to the second base plate, each lead screw rotatable but longitudinally fixed relative to the first and second base plates;
a collar disposed in threaded engagement about each of the lead screws, each collar configured to translate longitudinally along a corresponding one of the lead screws in response to rotation of the corresponding lead screw; and
an articulation cable coupled to each of the collars such that translation of one of the collars tensions or un-tensions a corresponding one of the articulation cables; and at least one biasing member disposed between the second base plate and the fixed plate to bias the portion of the actuation assembly proximally relative to the housing and the shaft, thereby biasing the articulation cables proximally to apply a pre-tension thereto.

8. The robotic surgical instrument according to claim 7, wherein the plurality of lead screws includes four lead screws arranged in a generally square cross-sectional configuration.

9. The robotic surgical instrument according to claim 7, further comprising at least one guide dowel extending between the first and second base plates and coupled with at least one of the collars to inhibit rotation of the at least one collar.

10. The robotic surgical instrument according to claim 9, wherein each collar includes at least one C-shaped channel, the at least one C-shaped channel of each collar configured to receive a portion of the at least one guide dowel therein to inhibit rotation of each collar.

11. The robotic surgical instrument according to claim 7, wherein the at least one biasing member is disposed about the shaft.

12. The robotic surgical instrument according to claim 7, wherein the at least one biasing member is centered relative to the plurality of lead screws to substantially equally pre-tension the articulation cables.

13. The robotic surgical instrument according to claim 7, wherein the at least one biasing member is a coil compression spring.

14. An articulation assembly for a robotic surgical instrument, comprising:
first and second base plates;
a plurality of lead screws extending distally from the first base plate to the second base plate, each lead screw rotatable but longitudinally fixed relative to the first and second base plates;
a collar disposed in threaded engagement about each of the lead screws, each collar configured to translate longitudinally along a corresponding one of the lead screws in response to rotation of the corresponding lead screw;
an articulation cable coupled to each of the collars such that translation of one of the collars tensions or un-tensions a corresponding one of the articulation cables; and
a biasing member disposed coaxially about each of the lead screws between the corresponding collar and the second base plate, each biasing member configured to bias the corresponding collar proximally relative to the second base plate, thereby biasing the articulation cables proximally to apply a pre-tension thereto.

15. The articulation assembly according to claim 14, wherein the plurality of lead screws includes four lead screws arranged in a generally square cross-sectional configuration.

16. The articulation assembly according to claim 14, further comprising at least one guide dowel extending between the first and second base plates and coupled with at least one of the collars to inhibit rotation of the at least one collar.

17. The articulation assembly according to claim 16, wherein each collar includes at least one C-shaped channel, the at least one C-shaped channel of each collar configured to receive a portion of the at least one guide dowel therein to inhibit rotation of each collar.

18. The articulation assembly according to claim 14, wherein the biasing members are similar to one another such that the articulation cables are substantially equally pre-tensioned.

19. The articulation assembly according to claim 14, wherein the biasing members are coil compression springs.

\* \* \* \* \*